(12) United States Patent
Craig

(10) Patent No.: US 7,353,657 B2
(45) Date of Patent: Apr. 8, 2008

(54) CONTROL OF LIQUID DROPLET STREAM WITH FLOW NEBULIZER

(76) Inventor: H Randall Craig, 3200 N. Dobson Rd., #F-7, Chandler, AZ (US) 85224

( * ) Notice: Subject to any disclaimer, the term of this patent is extended or adjusted under 35 U.S.C. 154(b) by 315 days.

(21) Appl. No.: 10/595,006

(22) PCT Filed: Apr. 6, 2005

(86) PCT No.: PCT/IB2005/051132

§ 371 (c)(1),
(2), (4) Date: Dec. 9, 2005

(87) PCT Pub. No.: WO2005/096698

PCT Pub. Date: Oct. 20, 2005

(65) Prior Publication Data

US 2007/0044487 A1    Mar. 1, 2007

Related U.S. Application Data

(60) Provisional application No. 60/560,183, filed on Apr. 6, 2004.

(51) Int. Cl.
F25D 13/06 (2006.01)
F25D 17/02 (2006.01)
F25C 1/00 (2006.01)
B05B 7/04 (2006.01)

(52) U.S. Cl. ..................... 62/63; 62/64; 62/74; 62/347; 239/434.5

(58) Field of Classification Search .................... 62/63, 62/64, 69, 100, 107, 169, 425, 347, 74; 239/434.5
See application file for complete search history.

(56) References Cited

U.S. PATENT DOCUMENTS

| | | | |
|---|---|---|---|
| 4,258,075 A | | 3/1981 | Hendricks |
| 4,313,745 A | * | 2/1982 | Kendall, Jr. ................. 65/21.4 |
| 4,748,817 A | | 6/1988 | Oura |
| 4,754,610 A | * | 7/1988 | Knodel et al. ................. 62/74 |
| 5,219,746 A | * | 6/1993 | Brinegar et al. ............... 435/6 |
| 5,666,821 A | | 9/1997 | Foster et al. |
| 5,682,759 A | * | 11/1997 | Hays ........................... 62/402 |
| 5,785,581 A | | 7/1998 | Settles |
| 6,223,542 B1 | | 5/2001 | Jones et al. |
| 6,381,967 B1 | * | 5/2002 | Craig ............................ 62/64 |
| 6,702,523 B1 | | 3/2004 | Docheff, III et al. |
| 2004/0250562 A1 | * | 12/2004 | Adiga et al. ............... 62/259.2 |

* cited by examiner

*Primary Examiner*—William C Doerrler
(74) *Attorney, Agent, or Firm*—Oppedahl Patent Law Firm LLC

(57) ABSTRACT

A controlled stream of droplets, including liquid droplets contained within an atomized or nebulized stream, are directed toward or onto a target. The target may be a measuring instrument, a gas or mixture of gases, or a solid, liquid, or slush surface. A particularly promising application of this invention is the generation and control of a high speed stream of small liquid droplets directed against a cryogenic surface resulting in very rapid freezing of the droplets. This rapid droplet freezing device would have numerous commercial, industrial, and research applications.

53 Claims, 18 Drawing Sheets

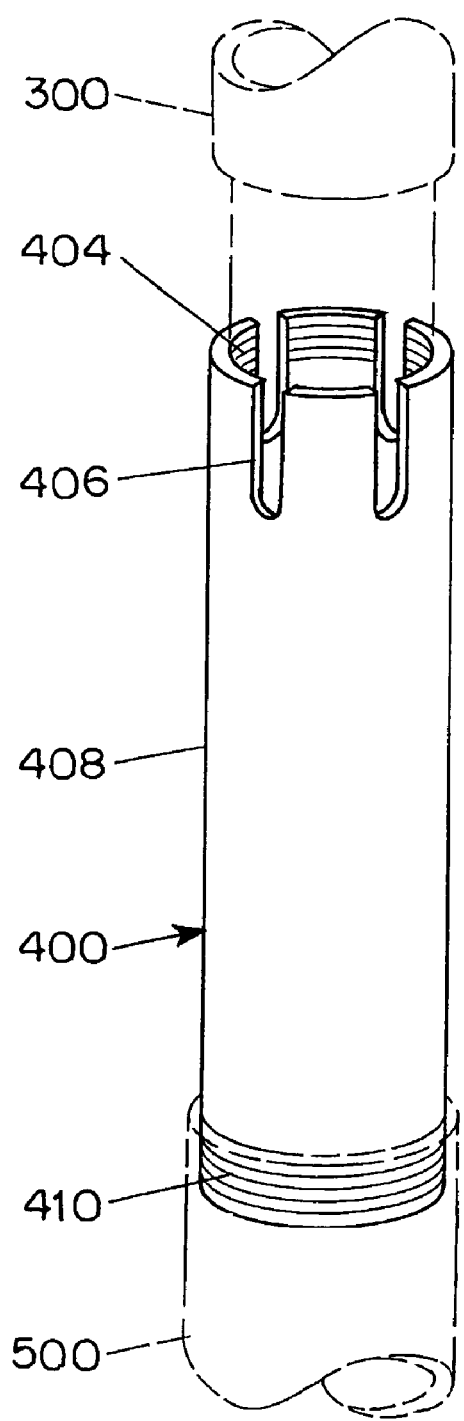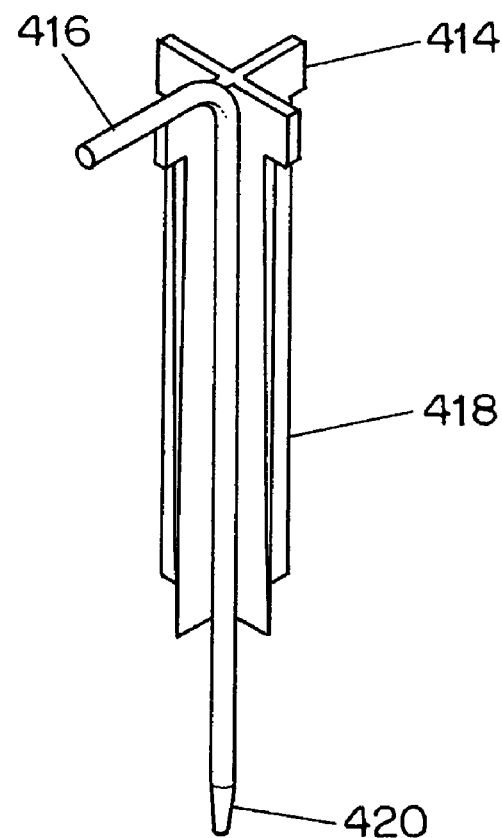
FIG. 4A
FIG. 4B

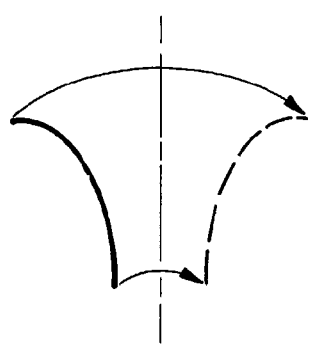 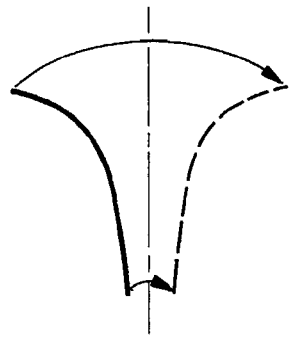 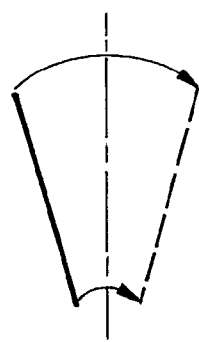
FIG. 12A    FIG. 12B    FIG. 12C
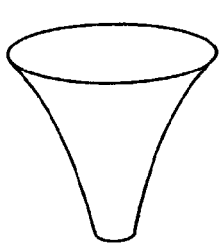 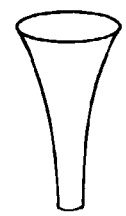 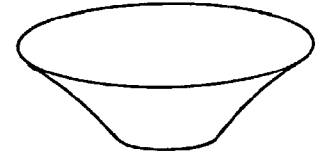 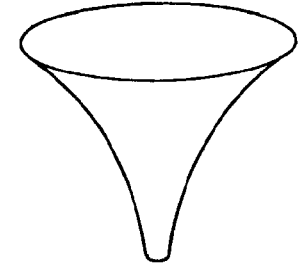
FIG. 12D    FIG. 12E    FIG. 12F    FIG. 12G
 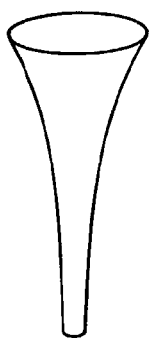 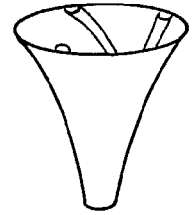 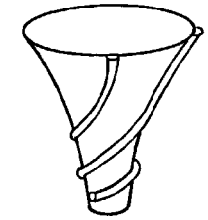 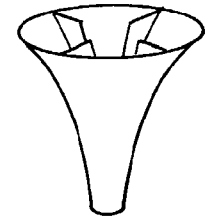
FIG. 12H           FIG. 12J    FIG. 12K    FIG. 12L
FIG. 12I
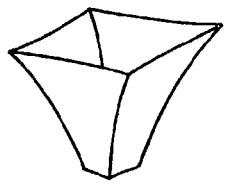 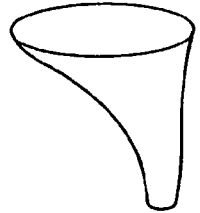 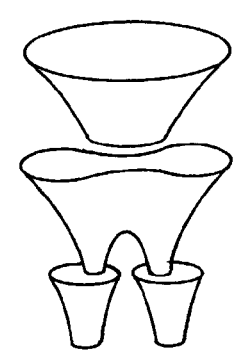 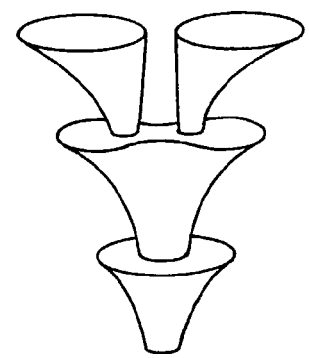
FIG. 12M    FIG. 12N    FIG. 12O    FIG. 12P

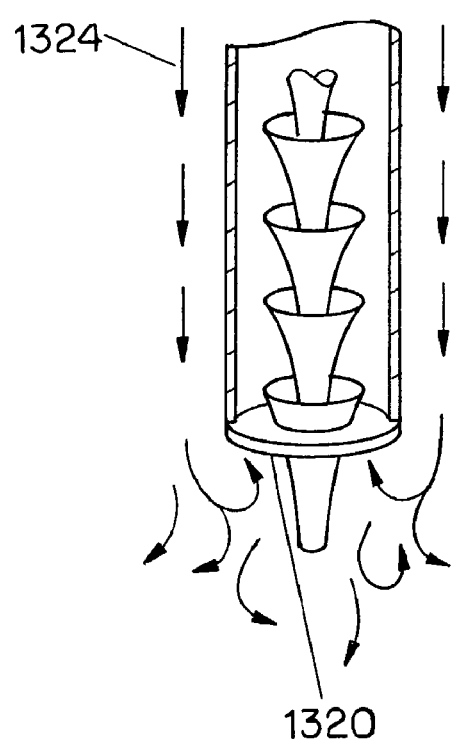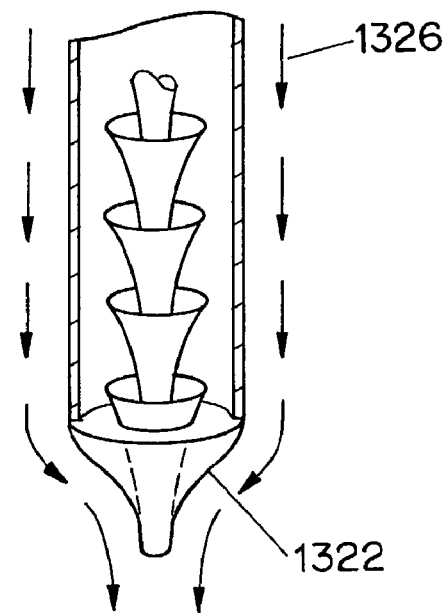
FIG. 13E
FIG. 13F

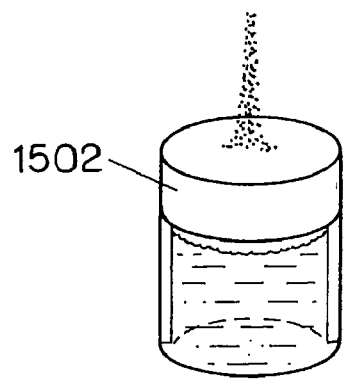
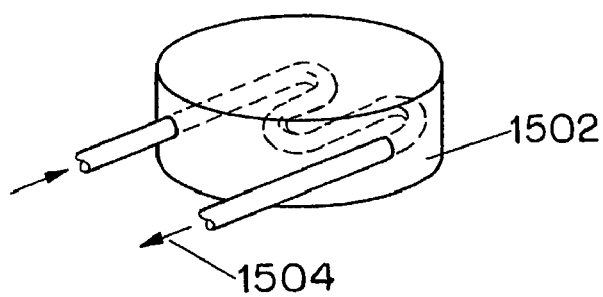
FIG. 15A    FIG. 15B
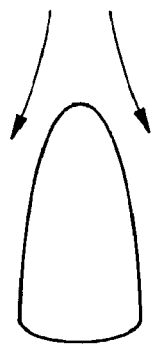
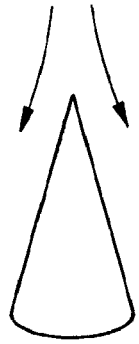
FIG. 15C    FIG. 15D
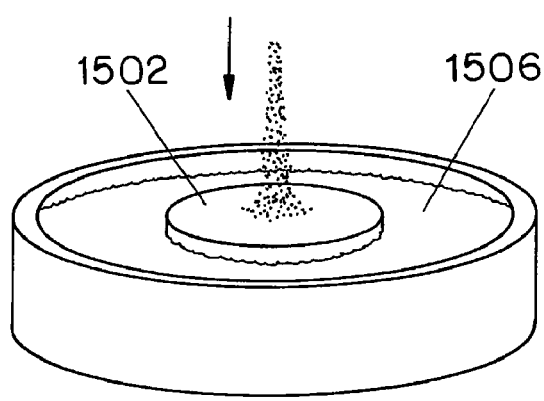
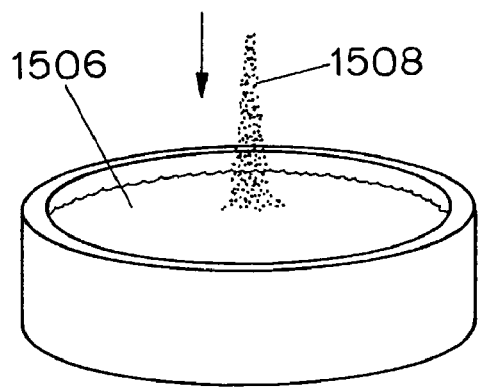
FIG. 15E    FIG. 15F

US 7,353,657 B2

CONTROL OF LIQUID DROPLET STREAM WITH FLOW NEBULIZER

CROSS-REFERENCE TO RELATED APPLICATIONS

This application claims the benefit of U.S. Application No. 60/560,183 filed Apr. 6, 2004, which application is hereby incorporated herein by reference for all purposes. U.S. Pat. No. 6,381,967 is also hereby incorporated herein by reference for all purposes.

BACKGROUND

For many years, the scientific community has had a strong desire to develop a method for preserving biological specimens for future use without compromising the utility of the specimen. This has become increasingly important for clinical and scientific applications which include preservation of human oocytes, frozen quarantines of donor eggs to prevent transmission of infectious diseases, long-term storage of embryos, and other preservation of biologic materials.

Common methods for preserving biological specimens often involve freezing the specimens. While some freezing methods have been successful others have had less positive results. Problems associated with current freezing methods include the formation of ice crystals, which may injure the specimens due to the sharp edges of the crystals, and toxicity introduced into the specimen as a result of the use of cryopreservation agents.

Documents with some relevance to this subject include: U.S. Pat. No. 6,381,967 and U.S. Pat. No. 6,702,523.

U.S. Pat. No. 6,381,967 relates to a method and apparatus for hyper-rapid freezing of liquid samples by converting the samples into droplets and rapidly driving the droplets directly onto the surface of a solid or slushed refrigerant. It is desirable to be better able to control the velocity and acceleration of the droplets as they are driven on to a refrigerant target. If constant acceleration could be achieved, fragile liquid samples such as biological material or living cells would preserve their integrity as they would be subjected to relatively low gravitational forces.

SUMMARY OF THE INVENTION

One embodiment of a method of the invention involves generating a very rapid velocity stream of nebulized particles. The stream of nebulized particles then impact a target or cryogenic surface to achieve an extremely high temperature gradient at the impact point. In the process, a column of driving gas is utilized to sequentially increase the velocity of a nebulized droplet stream. The target or cryogenic surface refrigerant is at least partially solidified. It may be undergoing a solid-to-liquid phase change, or a solid-to gas phase change. This method is especially useful for substances that are susceptible to ice crystal or osmotic damage, such as proteins, peptides, and other macromolecules.

Another embodiment of the invention is comprised of a mechanical assembly that directs a laminar flow of gas around a device that produces droplets or nebulized droplets of liquid in a relatively slow gas stream. The droplets in the gas stream are then accelerated to higher velocities as a narrow stream of droplets are directed against a cryogenic target.

An additional embodiment of the invention is illustrated in the schematic representation of FIG. 1. This basic assembly is comprised of a compressed or blown "driving gas" which is passed through an optional high flow filter to remove particulate matter, then directed through a humidifier to produce a water saturated atmosphere. It is then directed through an initial flow valve proximal to the freezing assembly which controls the volume and velocity of gas to the freezing assembly. The freezing assembly is comprised of a gas stream directional section which feeds into a laminar flow section, and the gas stream acquires the nebulized droplets within or immediately after this section. The droplet gas stream is then directed through an accelerator section, where the liquid droplets are accelerated to a high velocity and condensed into a narrow stream. This droplet stream is then directed into a freezing section which contains a solid, liquid, or slushed cryogenic surface or other target, with directional control of the droplet stream provided by gas flow collectors located circumferentially around the cryogenic surface.

After leaving the freezing assembly, the gas stream passes into ambient atmosphere or through a control valve to a vacuum fan or vacuum oriented atmosphere, with volume and velocity of the exhaust flow controlled by the post-freezing assembly valve.

There are several optional embodiments of the invention. For example, each of the components located proximal to the freezing assembly or distal to the freezing assembly are not necessary. For instance, the freezing assembly can be attached directly to a compressed gas source without use of a high flow filter, humidifier, or control valve, and without the use of any components beyond the freezing assembly. Alternately, a flow filter, humidifier, or control valve can be added in any combination in front of the freezing assembly. Any method which will produce a pressure gradient through the freezing assembly can be used as the source of gas flow, including a compressed gas tank, fan, turbine, or piston based assembly. Ultimately, the proximal end of the freezing assembly can be opened to ambient atmosphere, with the pressure gradient generated instead by application of a vacuum at the end of the freezing assembly, with the vacuum produced by any method including a vacuum fan, depressurized tank, or piston assembly. The highest level of pressure gradient control across the freezing assembly would be obtained by adding the above control methods both proximal and distal to the freezing assembly, with the required degree of control of the assembly dependent upon the specific application requirements of the device.

BRIEF DESCRIPTION OF DRAWINGS

FIG. 4A is an illustration of one embodiment of the laminar flow vane section.

FIG. 4B is an example of one embodiment of a laminar flow vane.

FIG. 6A is an illustration of one embodiment of the droplet freezing section.

FIGS. 12A-12P illustrate several embodiments of accelerator cones.

FIGS. 13A-13F illustrate variations in the control of the acquired ambient gas for the freezing section.

FIGS. 15A-15J illustrate several embodiments of the target.

DETAILED DESCRIPTION

Definitions

Figure 1:
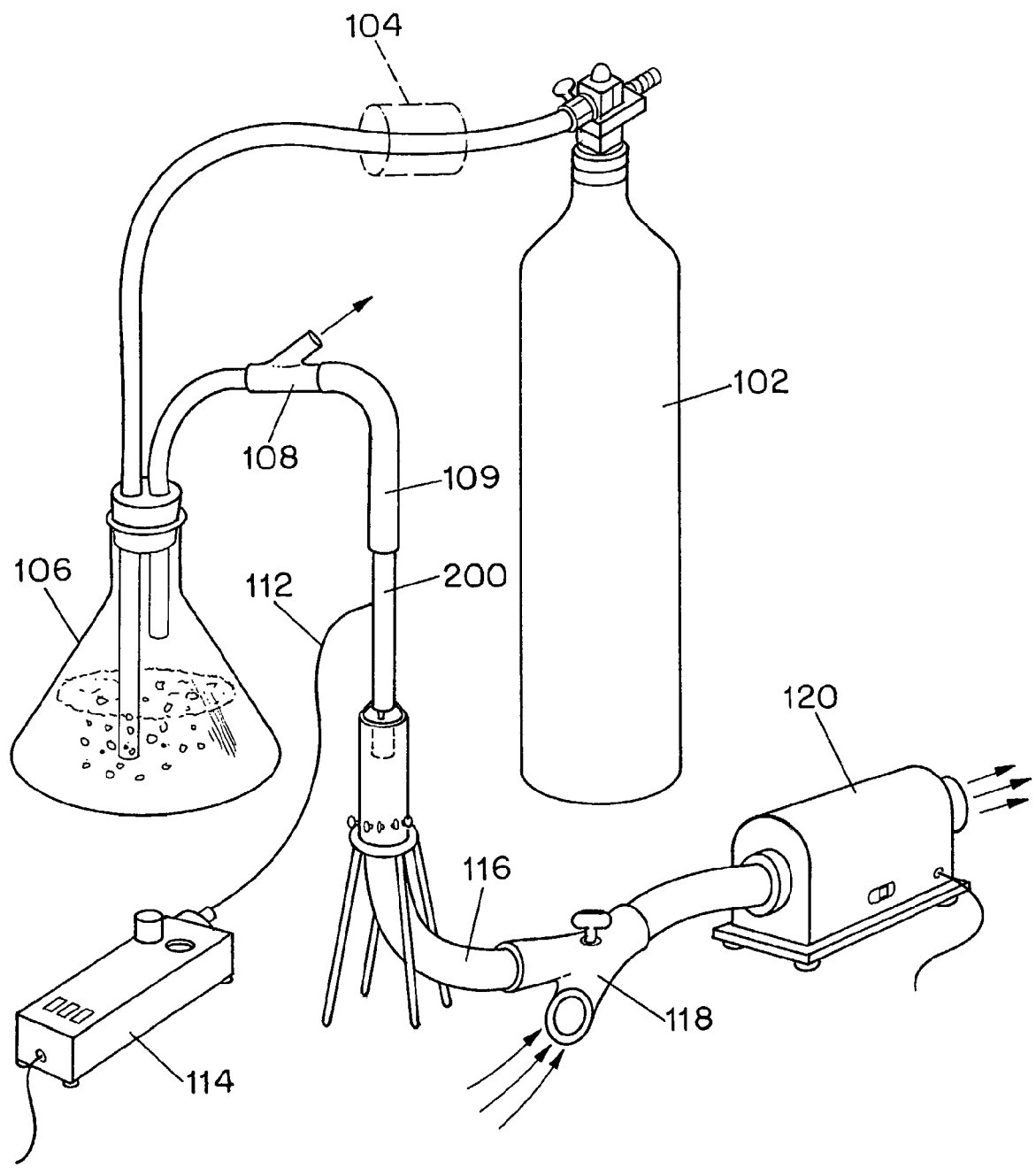
FIG. 1 is an illustration of the basic assembly of one embodiment of the invention.

For the purposes of the present invention, the following terms shall have the following meanings.

A large number of substances can be employed as the refrigerant, depending on the temperature range desired and the composition of the liquid drops to be frozen. It should be understood that "refrigerant" includes substances with a temperature less than or equal to 0 degrees Celsius. When two or more refrigerants are used, the entire system has a temperature less than or equal to 0 degrees Celsius. Refrigerants can be selected from several basic types, including chemical elements and compounds, organic substances or mixtures of these items. Examples of elements include helium (under pressure), hydrogen, nitrogen, argon, neon, krypton, xenon, oxygen, mercury, gallium, and lead. An example of a compound is water and carbon dioxide (under pressure). Examples of organic substances include propane, benzene, ethanol, methanol, and Freon. Mixtures of two or more elements and/or compounds mixed together to alter melting temperature or other physical characteristics can also be used as the refrigerant; e.g. Water+NaCl→Brine, Oxygen+Nitrogen→Slushed/Solid Air, Ethane+Propane.

Any substance or compound can be used as the refrigerant for this freezing method as long as it can rapidly absorb heat from liquid droplets by its phase change from solid to partially solidified to liquid. The melting temperature of the refrigerant must be lower than the liquid droplet freezing temperature, and the heat of fusion absorbed by the refrigerant (along with some additional heat absorbed by the liquefied refrigerant in some cases) must be greater than the heat of fusion released by the freezing liquid droplets.

A variation of this freezing method involves the use of sublimating compounds as the refrigerant. The phase change from solid to liquid is the basic process for absorption of heat from freezing droplets, but the phase change from solid to gas of the refrigerant can also be used. An example is spraying nebulized liquid droplets directly onto or into the surface of solid carbon dioxide. A disadvantage of this method is the generation of an insulating gas layer around the droplets, which may slow the rate of freezing. This disadvantage can be overcome using devices that rapidly drive the liquid droplets into the solid refrigerant in order to maintain direct contact between their surfaces.

The phase change of the refrigerant from solid to at least partially solidified is a key element of this process. The phrase "at least partially solidified" is intended to encompass completely solid and slush phases. The term "slush" is intended to encompass liquid that has just begun to solidify through equal parts solid and liquid up to the point just before complete solidification. In a slush, the ratio of solid to liquid components is such that movement of particles of solid is controlled by the liquid component. The solid and liquid components of a slush may be the same element or compound or may be different elements or compounds. A slush includes stable mixtures of liquid and solid substantially at equilibrium. When the solid and liquid components are different elements or compounds, the elements or compounds must be compatible in terms of providing an environment suitable for freezing the sample.

The production of solid or slushed refrigerants, especially in the cryogenic temperature range, requires mechanical means or a secondary refrigerant. The mechanical means may be in the form of a refrigeration means or a vacuum chamber. Liquid refrigerant is placed in a vacuum chamber and placed under partial vacuum to achieve at least partial solidification of the refrigerant. The secondary refrigerant can be any heat-absorbing substance held at a temperature lower than the freezing point of the primary refrigerant. A secondary refrigerant is used to freeze the primary refrigerant into a solid or slushed state either by direct contact or by indirect contact through a container. Freezing of the primary refrigerant may be a one-time single event, or can occur as a repetitive or continuous renewal process. Selection of appropriate primary and secondary refrigerants results in production of an optimal slushed primary refrigerant or may be used to change the working temperature of the primary solid refrigerant to maximize liquid droplet freezing rates. For example, frozen argon held at the temperature of liquid helium will absorb much more heat more rapidly from liquid droplets than frozen argon held at liquid nitrogen temperature. Because of the wide range of freezing temperatures for various elemental, compound and organic refrigerants, numerous combinations of primary and secondary refrigerants are possible. The secondary refrigerant for one rapid-freezing application can be used as a primary refrigerant for another application. Several examples of primary and secondary refrigerants are provided in Table 1 of U.S. Pat. No. 6,381,967.

The physical size of the sample liquid droplets to be frozen has a significant influence on the freezing rate achieved by this method. In general, the smaller the liquid droplet, the faster it will freeze. Nebulizer type and control can be used to obtain optimal drop or droplet sizes for individual applications of the freezing method. In general, optimum droplet sizes would range from 50 to 700 microns.

A large number of nebulizing, atomizing and vaporizing devices using different operating principles are available, any of which can be used to produce liquid droplets in a variety of sizes and rates for this freezing process. These include spray nozzles, pressurized small apertures, gas driven nozzles, fine screen methods, ultrasonic devices, and drip nozzles. Selection of an appropriate device depends on the specific freezing application and desired drop size, e.g. biological or fragile specimens may be damaged by some nebulizers and may require more gentle types such as glass-fret or fine screen nebulizers. Examples of what the droplets may contain include: human egg cells or oocytes, sperm, red blood cells, embryos, and proteins. The content of the droplet minus the biological material could be various substances including: distilled water, non-distilled water, glycol, saline, salt solutions, and other substances that are relatively isotonic with whatever is in the biological material that is desired to be preserved.

A flow cytometer can also be used for producing liquid droplets of specific sizes. A flow cytometer can be used to achieve individual drops containing a single cell, or specific numbers of cells. The amount of fluid per cell can also be controlled to achieve optimal freezing conditions which provide for optimal viability upon thawing. The flow cytometer may be communicatively coupled to a container containing a suspension of biological material to be frozen.

The liquid droplet heat of fusion and droplet-to-primary refrigerant temperature gradient are the factors determining the total amount of heat to be removed from the droplet to achieve complete freezing. The rate of freezing depends on these factors and the specific heat and the thermoconductivity of the droplet and the primary refrigerant. The freezing rate can be altered by lowering the initial temperature of the droplets, or by changing the heat of fusion by adding solutes. For example, most biological specimens in liquid solutions can be precooled to within a few degrees above the freezing point without significant damage, which would reduce the total amount of heat to be removed from the liquid droplets and increase the rate of freezing at the time of contact with the primary refrigerant.

Cryopreservatives may be added to the liquid samples to improve the survival of biological or other specimens. For freezing rates that do not achieve vitrification of the sample, ice crystal or frozen crystal sizes can be minimized by the addition of a cryopreservative.

Basic Assembly

Figure 2:
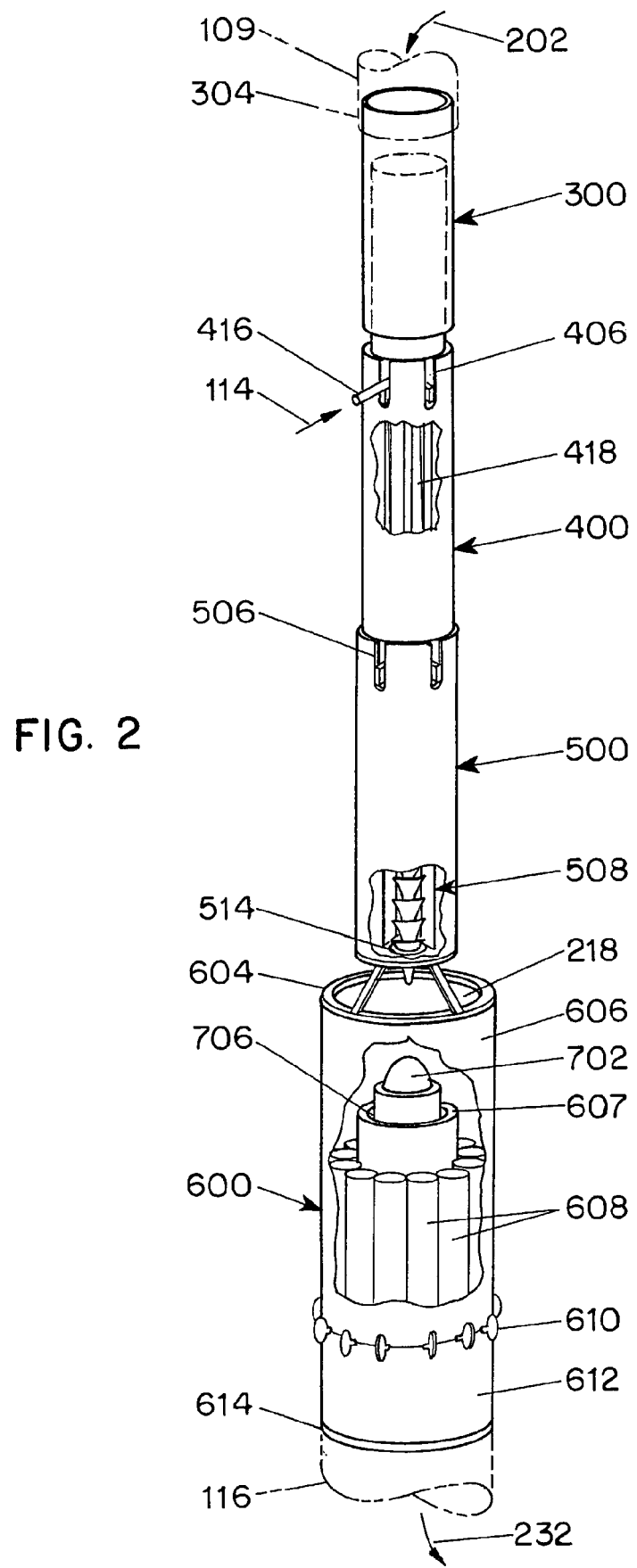
FIG. 2 is an illustration of one embodiment of the freezing assembly.

A schematic representation of an embodiment of the invention is illustrated by the basic assembly in FIG. 1. This embodiment is comprised of a compressed or blown "driving gas" (102), controlled by a regulator valve, which is then passed through an optional high flow filter (104) to remove particulate matter. The gas is then directed through a humidifier (106) to produce a water saturated atmosphere. It is then directed through an initial flow valve (108), proximal to the freezing assembly (200), which controls the volume and velocity of gas to the freezing assembly. The freezing assembly (200) as illustrated by FIG. 2 is comprised of a gas stream directional section (109) which feeds into a laminar flow section (400). The gas stream acquires the nebulized droplets prior to, within, or immediately after this laminar flow section. The droplet gas stream is then directed through an accelerator section (500), where the liquid droplets are accelerated to a high velocity and condensed into a narrow stream. This droplet stream is then directed into a freezing section which contains a solid, liquid, or slushed cryogenic surface or other target (702), with directional control of the droplet stream provided by gas flow collectors (608) located circumferentially around the cryogenic surface (702).

After leaving the freezing assembly, the gas stream passes into ambient atmosphere (232) or through a control valve (118) to a vacuum fan (120) or vacuum oriented atmosphere, with volume and velocity of the exhaust flow controlled by the post-freezing assembly valve (118). A vacuum hose (116) may serve as a connection between the freezing assembly (200) and the vacuum flow valve (118).

Each of the components located proximal to the freezing assembly (200) or distal to the freezing assembly (200) are optional. For instance, the freezing assembly (200) can be attached directly to a compressed gas source (102) without use of a high flow filter (104), humidifier (106), or control valve (108), and without the use of any components beyond the freezing assembly (200). Alternately, a flow filter (104), humidifier (106), or control valve (108) can be added in any combination in front of the freezing assembly (200). Any method which will produce a pressure gradient through the freezing assembly (200) can be used as the source of gas flow, including a compressed gas tank (as illustrated in FIG. 1), fan, turbine, or piston based assembly. Ultimately, the proximal end of the freezing assembly can be opened to ambient atmosphere, with the pressure gradient generated instead by application of a vacuum at the end of the freezing assembly. The vacuum may be produced by any method including a vacuum fan (120), depressurized tank, or piston assembly. The highest level of pressure gradient control across the freezing assembly (200) would be obtained by adding the above control methods both proximal and distal to the freezing assembly (200), with the required degree of control of the assembly dependent upon the specific application requirements of the device.

One of the advantages of the apparatus of this invention is that most embodiments are relatively inexpensive to assemble. The tubing, piping, and or hose pieces used to construct each section may be made out of many different materials including: metal, plastic, glass, rubber, and other similar substances which would be sufficient to contain liquids and gasses at relatively low pressures.

Freezing Assembly

A more detailed schematic of one embodiment of the freezing assembly (200) is provided in FIG. 2. A gas pressure gradient is applied across the freezing assembly, with high gas pressure (202) at the upper end of the device, low gas pressure at the lower end of the device (232), and the ambient air pressure typically between the pressure gradient values. Any gas can be used as the driving gas for this device, with nitrogen (102) used in the example provided in FIG. 1. Other driving gases include air, oxygen, hydrogen, helium, argon, carbon dioxide, or any other available commercial or industrial gas mixture. The gas may flow into the freezing assembly through a pressurized gas hose (109) coupled to the assembly with hose coupling (304). Coupling the hose to the assembly may be accomplished by various methods including: simply sliding the hose over the assembly allowing friction to keep the hose in place, placing a simple clamp over the hose to further secure it into place, or even adding a sticky substance between the hose and the assembly. In general, any means which would keep the hose in place to avoid gas leaking out between the hose and the assembly wold be sufficient for the hose coupling. In one embodiment of the invention, the pressurized gas hose (109) is water vapor saturated. As the gas flows down through the freezing assembly (200), it passes through the gas stream directional section (300) first, and then into the laminar flow vane section (400) where it acquires the nebulized or droplet sample at or near the middle of the gas stream. In the embodiment illustrated, the droplet sample is acquired from a powered syringe or flow cytometer (114). The gas stream then passes from the laminar flow vane section through a tapered nozzle (420) and then through the nebulized droplet collimator and accelerator section (500) where the entire stream is narrowed to a smaller diameter resulting in increased gas stream velocity. The high velocity laminar flow gas stream exits the accelerator section (500), containing at its center a high velocity, very narrow nebulized droplet stream which is then directed into the freezing section. At this point, the gas stream may acquire an ambient gas or air intake (218) which may allow greater control of the direction of the nebulized droplet stream. The nebulized droplets then are driven rapidly onto the cryogenic surface (702), in this example a frozen solid argon or nitrogen plug. Other cryogenic surfaces may include frozen gases, chilled metallic, ceramic, or plastic surfaces, liquid nitrogen, liquid helium, liquid argon, or other liquified or slush cryogenic gases. The nebulized sample droplets are rapidly frozen upon contact with the cryogenic surface (702), and then are collected from the surface or from the surrounding pool of melted cryogen (706) in the form of small frozen particles or droplets. The gas column surrounding the nebulized stream is directed by the cryogenic surface outward to the periphery of the freezing assembly (200), where it was then collected by the parallel radial ambient stream cylinders or channels (608). This particular embodiment of the invention requires eight to twelve tubes or cylinders or channels (608). FIG. 2 also illustrates the liquified cryogen container rim (607)

The rate and volume of gas flow through these ambient stream collectors (608) are individually controlled with directional stream control valves (610) so that the moving gas column can be shifted back and forth within the freezing assembly (200). This has the effect of shifting the impact point of the nebulized droplet stream on the cryogenic surface (702). This allows fine tuning of the droplet stream to obtain optimal freezing contact with the cryogenic surface (702).

The circumferential gas stream passes through the ambient stream collectors (608) and into either the ambient atmosphere or the vacuum hose (116) at the bottom of the freezing assembly (200). The vacuum hose in this particular embodiment is coupled to the ambient stream collectors (224) with house coupling (228). Additional control of the gas stream can be exercised by adjusting the gas pressure at the lower end of the freezing assembly (200).

Freezing Assembly Sections

Embodiments of the individual sections of the freezing assembly (200) will be discussed in greater detail in the following paragraphs.

Directional Section

Figure 3:
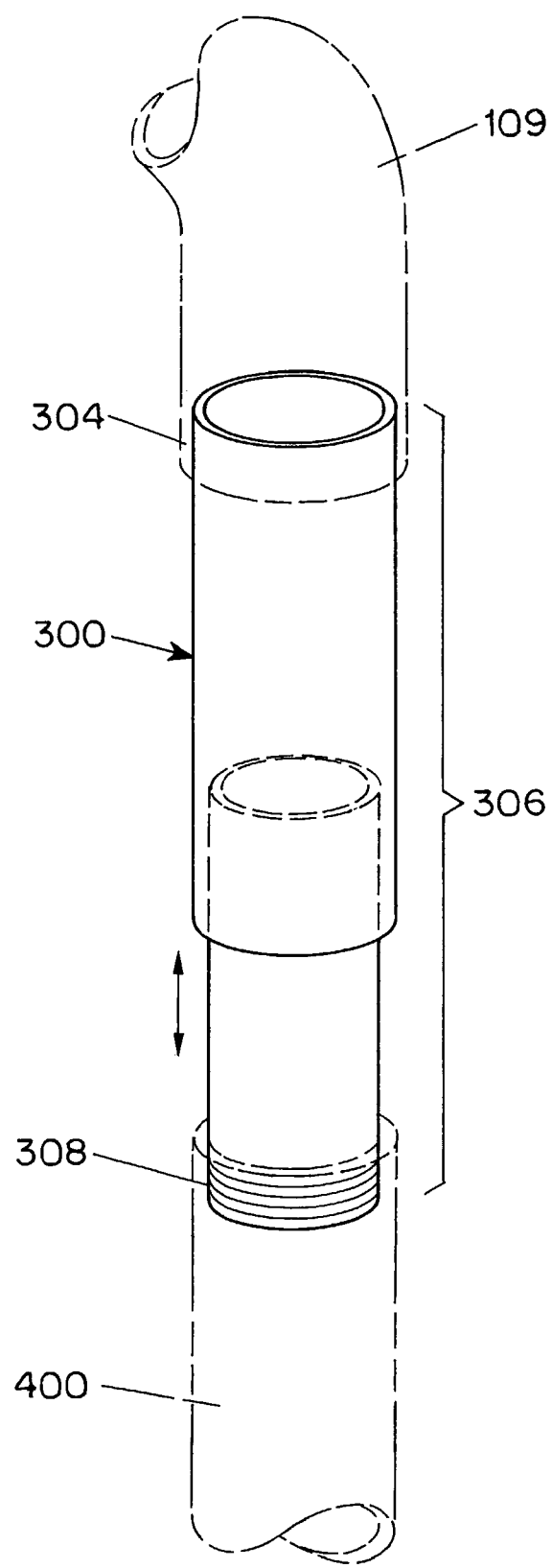
FIG. 3 is an illustration of one embodiment of a gas stream directional section with a "trombone" variable length.

An embodiment of the gas stream directional section (300) is illustrated in FIG. 3. This section connects the pressurized gas source (103) to the laminar flow section (400). The pressurized gas hose (109) is coupled with the gas stream directional section with the house coupling (304). In this illustration, a sliding trombone design (306) or telescoping design is used to change the length of the directional section (300) to provide optimal gas flow to the freezing assembly (200) below. Chaotic and nonlaminar gas flow will likely pass through this section, and altering the length of the section may permit better delivery of more organized flow to the laminar flow section (400). FIG. 3 illustrates an embodiment of the invention where external threads (308) are used to connect the gas stream directional section (300) to the laminar flow vane section (400). However, other means may be used to connect the two sections together depending on what is appropriate for the type of material used for each section.

Laminar Flow Section

An embodiment of the laminar flow vane section (400) is illustrated in FIG. 4A. It is designed to convert chaotic gas flow from the gas stream direction section (300) above to a laminar stream of gas flow as it exits into the accelerator section (500) below. This is done by insertion of flow vanes (418) into the section cylinder (408). Several types of flow vane assemblies (418) can be inserted in this section, with a four-vane radial design provided as an example in FIG. 4B. Other types of laminar devices (400) include radial vanes (418) with different numbers of arms, including three arms, four arms (as above), or five or more radial arms, with the advantage of having the liquid sample line (416) located at the center of the radial vane section (418) to minimize interference with the gas flow. Radial vanes (418) are not the only devices that would force laminar flow, other designs may include boxes or cylinders which viewed from above would appear as a grid, concentric circle "target", or combination of these designs. In addition, the vanes can be shaped in order to minimize turbulent or nonlaminar flow along their surface or after exiting the section, primarily by tapering the leading and trailing edge of the vanes to very small cross sectional areas. Tapered Nozzle (420) is illustrated in FIG. 4B. The embodiment of the invention illustrated in FIG. 4A also illustrates the internal threads (404) used to connect the laminar flow vane section (400) to the gas stream directional section (300). The external threads (410), used to connect the laminar flow vane section (400) to the collimator and accelerator section (500), are illustrated as well. Cylinder notches (406) are shown on the section cylinder and are provided to support the vanes (418) by allowing the shelf for cylinder notch (414) to rest upon them. Other means besides the internal threads (404) may be used to connect the laminar flow vane section to the gas stream directional section. The connection means can be what ever is appropriate for the type of material used for each section. This includes reversing the size of the two sections so that the external threads could instead be placed on the accelerator section and the internal threads on the laminar flow vane section.

Collimator and Accelerator Section

Figure 5A:
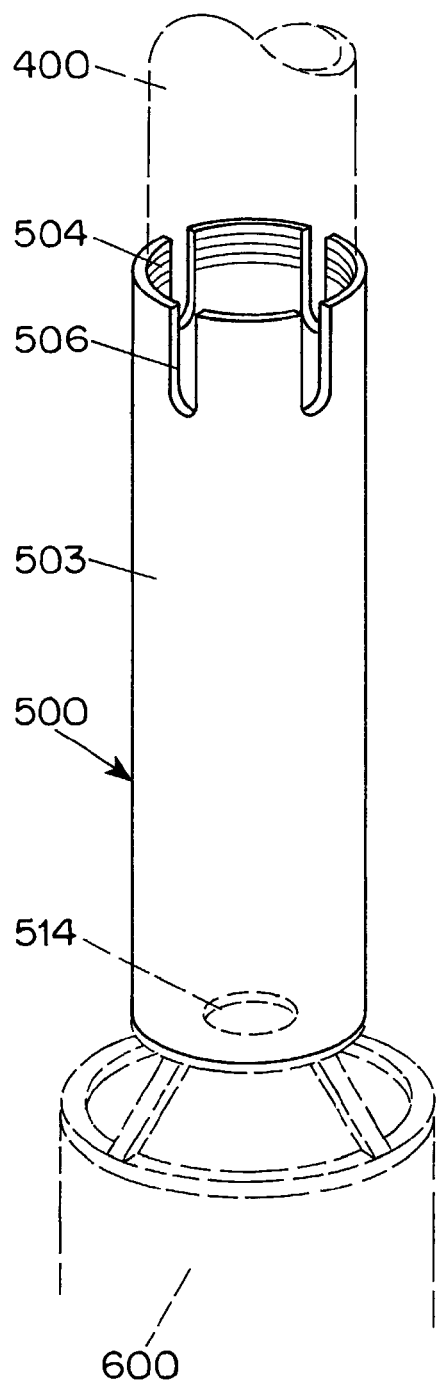
FIG. 5A is an illustration of one embodiment of the collimator and accelerator section.
Figure 5B:
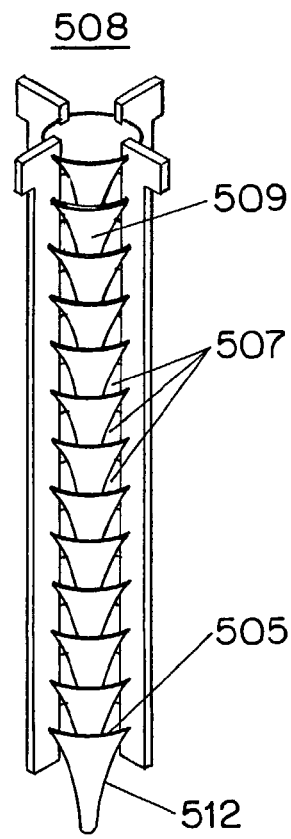
FIG. 5B is an illustration of one embodiment of a stack cone assembly.

An embodiment of the accelerator section (500) is illustrated by FIG. 5A. This section (500) is comprised of a stacked cone assembly (508), which is illustrated in FIG. 5B, of open ended gas accelerator cones (512) loosely separated from each other, with the large end (511) of the cones (512) facing up toward the laminar flow vane section (400). The small end of the cones (513) faces down towards the droplet freezing section (600). One embodiment of a cone is shown by FIG. 5D. This particular embodiment of the accelerator section (500) shown in FIG. 5A has internal threads (504) which connect it to the laminar flow vain section (400). The carrier gas flow is directed along the outer part of the section, but because the lower end of the assembly is sealed off, all the carrier gas is eventually forced by the cones (512) into a stream which exits the narrow end of the bottom cone (514). The carrier gas enters the interior cone sections evenly along the length of the accelerator section (500), with some gas entering the large end of the top cone (509), and with incremental amounts of gas entering circumferentially between each subsequent cone spacing (507), until the last of the carrier gas enters the large end of the last cone section (505). This has the effect of increasing the interior central gas column velocity incrementally faster as it flows progressively down the section. A concentric layer of rapidly flowing gas is added to the outer circumference of the interior gas column as it passes through each cone on the way down the section.

The increase in the velocity of the gas column from the entry point to the exit point in this section is directly proportional to the ratio of the cross sectional area at the top of the section (calculated from the radius of the laminar flow vane section (400) above) to the circular cross sectional area of the narrow end of the lowest cone (calculated from the radius of the lowest cone exit point (514)). The entry gas velocity (and therefore the proportional exit gas velocity) also depends upon the pressure gradient across this section, and can be increased or decreased by changes in the entry gas pressure above or the exit pressure (or vacuum) below. Laminar flow is maintained at the top, throughout, and at the bottom of the section by spacing-vanes (510), illustrated in FIG. 5C which also serve to support and properly space the open ended cones (512). Good design also incorporates a tapered leading and trailing edge of each cone to minimize turbulence.

In one embodiment of the invention, the droplet or nebulized liquid stream enters the top of the accelerator section (500) as a relatively diffuse cloud at or near the middle of the wide end of the uppermost cone (509). This nebulized stream is then sequentially narrowed and accelerated to faster and faster velocity as it passes down through the column as it acquires outer concentric layers of carrier gas between each cone (512). By the time the gas stream exits the last cone (514), the nebulized droplet stream is concentrated into a very fast, very narrow stream at the center of the carrier gas column. A relatively constant acceleration is achieved with this device. Fragile liquid samples such as biological material or living cells will therefore be subjected to relatively low gravitational forces to preserve their integrity. The spacing of the accelerator cones does not necessarily have to be even, with increasing or decreasing spacing distances optional along the length of the column. This would allow increasing or decreasing acceleration of the gas stream down the column which may be appropriate for certain applications.

Figure 5C:
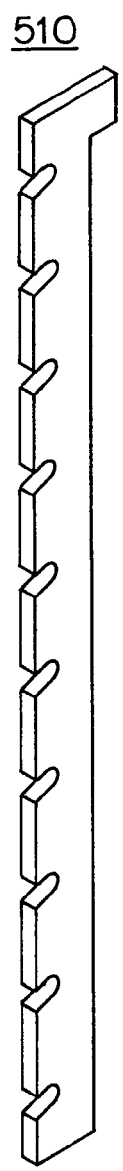
FIG. 5C illustrates an embodiment of a spacing vane.
Figure 5D:
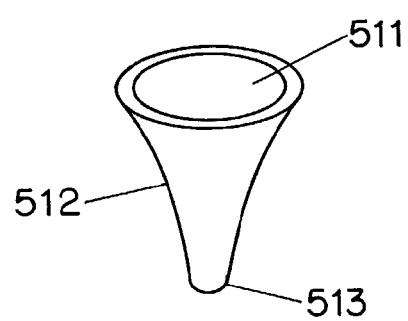
FIG. 5D illustrates an embodiment of an open ended cone.

The embodiment of the invention illustrated in FIGS. 5A, 5B and 5C include spacing vane (510), four of which are shown supporting and keeping the spacing of the stacked assembly (508) correct in FIG. 5B. The cylinder (503) of this embodiment of the invention has cylinder notches (506) which are designed to support the spacing vanes. The lowest cone opening (514) is also illustrated.

Droplet Freezing Section

An embodiment of the droplet freezing section (600) is illustrated in FIG. 6A, FIG. 6B, FIG. 6C, FIG. 7A and FIG. 7B. The primary function of this section is to provide a target (702) for the nebulized stream, with a secondary function of control of the direction of the nebulized stream and its subsequent impact point on the target (702). In the illustrated examples, the target is a plug of frozen cryogenic gas (for instance frozen argon). Other types of targets will be illustrated and described in FIG. 15. The nebulized stream enters the top of the droplet freezing section surrounded by the laminar flow driving gas, and may pick up an additional outer layer of moving laminar flow gas at the support spacer section (604). The droplet freezing section (600) inherits a relatively narrow driving gas stream which exits at the same diameter of the last gas accelerator cone (514). This narrow gas stream may enter a narrow droplet freezing section (600) with approximately the same diameter, or it may enter a droplet freezing section with significantly larger diameter and therefore encounter ambient gas at a different velocity. If the ambient gas is not moving then the carrier gas stream will spread and eventually break up into chaotic flow. To minimize this effect, the ambient gas at the top of the droplet freezing section (600) can be drawn in from an outside source (218) by pressure or vacuum and achieve an approximately equal velocity with the driving gas stream.

Figure 6B:
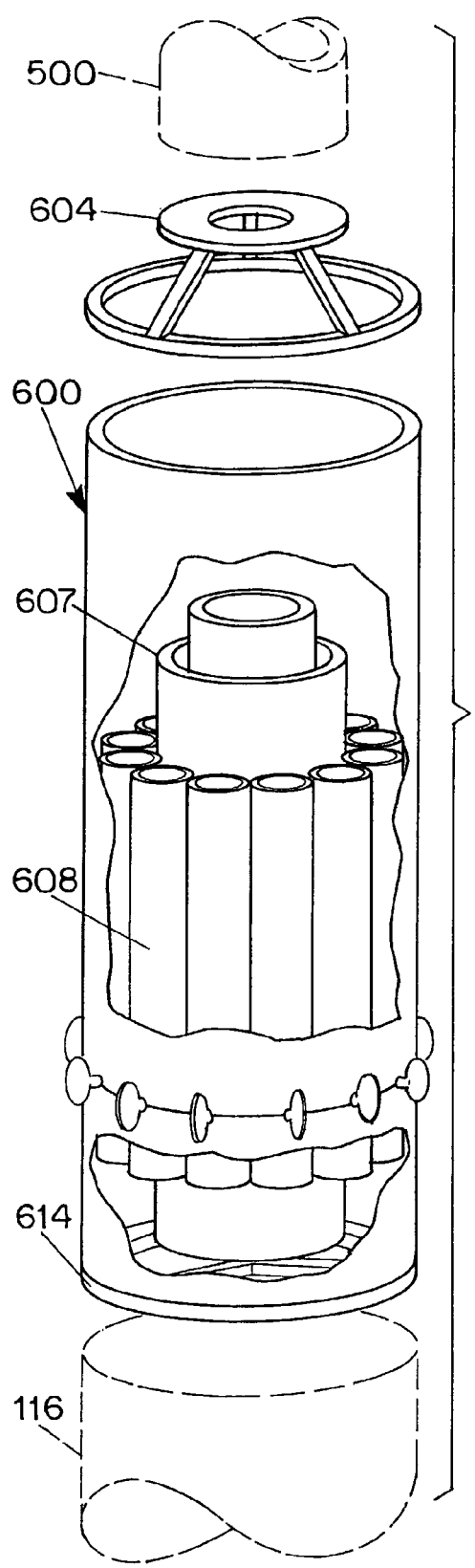
FIG. 6B illustrates an embodiment of a parallel radial ambient stream collector.
Figure 6B:
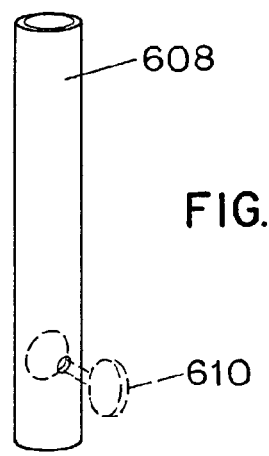

The ambient gas stream and the outer layers of the driving gas stream can be drawn away from the center of the stream at or above the point of target impact by radial gas collectors (608) within the droplet freezing section. The parallel radial ambient stream collector tubes (608) are illustrated in FIG. 6B. Differential control of the amount of flow through the radial gas collectors (608) can be used to move the driving gas stream and its internal nebulized stream in various directions in order to control the nebulized impact point on the target (702). In the illustrated example, individual control of the flow through the parallel radial ambient stream collector tubes (608) is done by directional stream control valve (610). This allows the nebulized droplet particles to directly impact into the target (701) while allowing the driving gas stream and the ambient gas stream to flow away from the nebulized stream at the impact point in a controlled fashion.

Figure 6C:
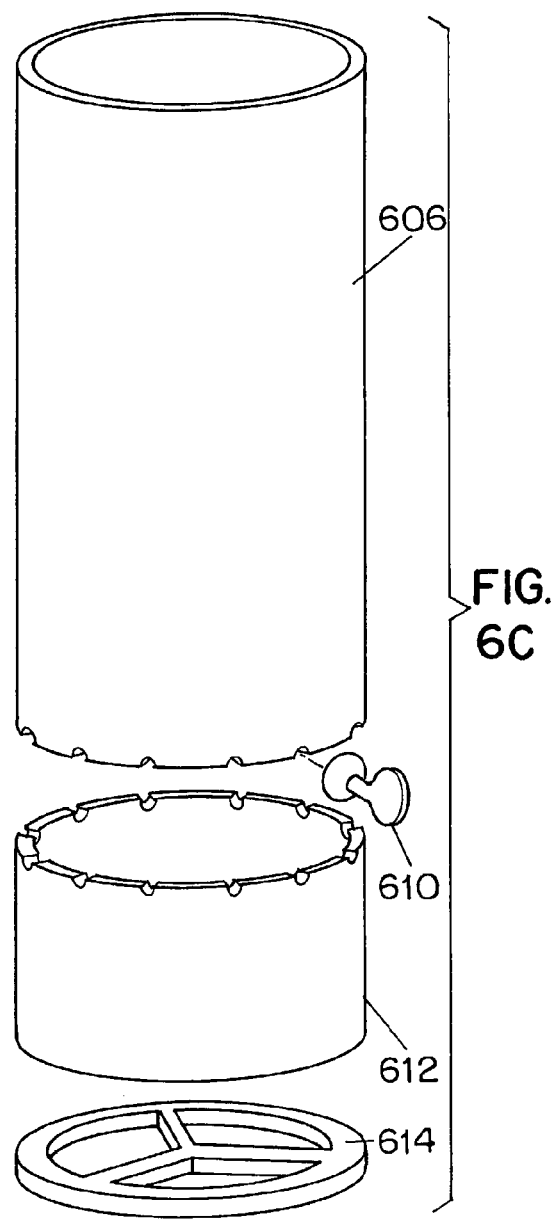
FIG. 6C illustrates an explosive view of an embodiment of a droplet freezing section.

The embodiment of the invention illustrated in FIG. 6C also includes the upper (606) and lower cylinders (612) of the droplet freezing section which are separated by notches (613) arranged in a radial pattern about the lower portion of the upper cylinder (606) and the upper portion of the lower cylinder (612). These notches are of sufficient size to allow the directional stream control valves (610) to pass through to radial ambient stream collectors (608) located inside the cylinders. FIG. 6C also includes an illustration of the cryogen container support (614) which is located below the lower cylinder and above vacuum hose (116).

Cryogen Container and Collector

Figure 7A:
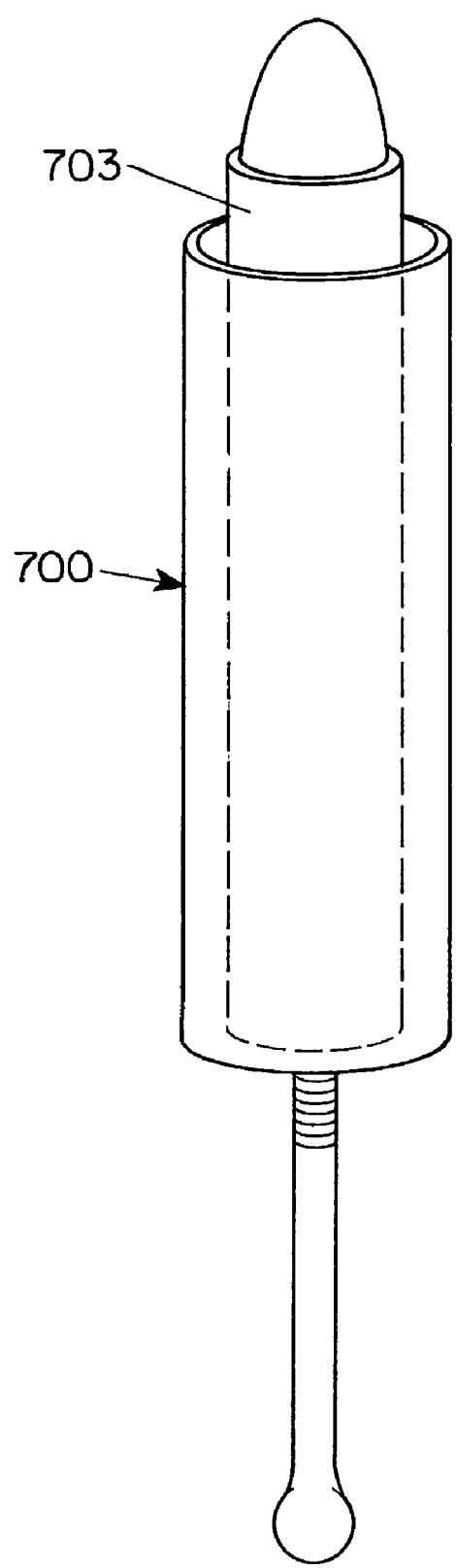
FIG. 7A is an illustration of one embodiment of the cryogen container and collector.
Figure 7B:
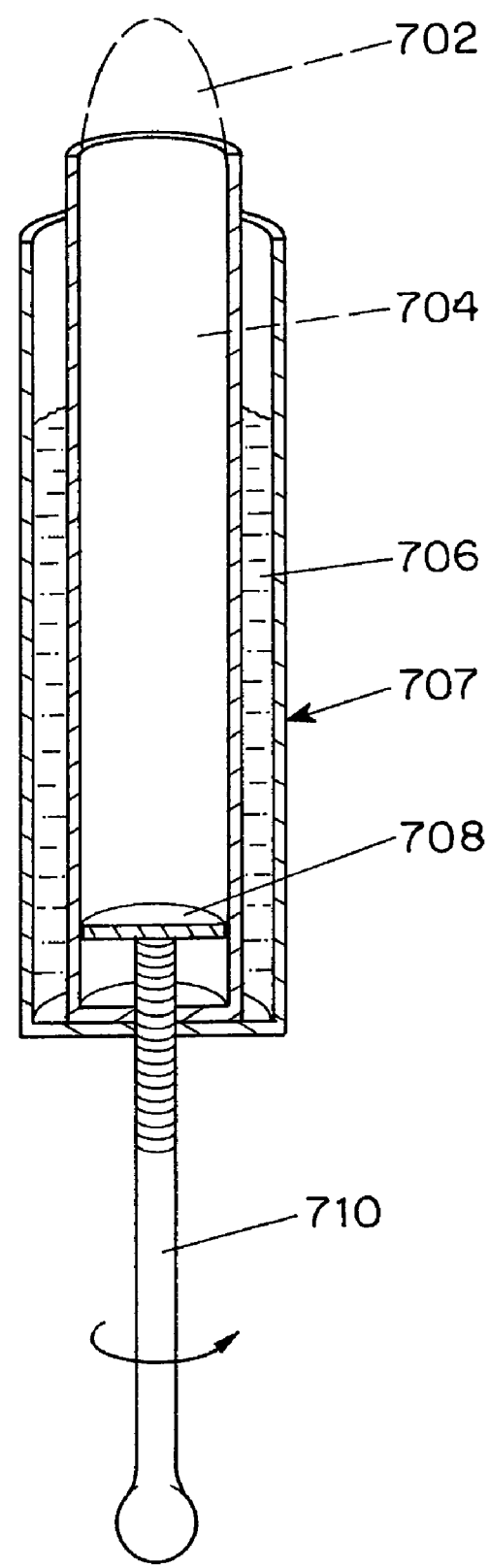
FIG. 7B is an illustration of one embodiment of the cryogen container and collector.

An embodiment of the cryogen container and collector is illustrated in FIG. 7A and FIG. 7B. In this particular version, a frozen cryogenic gas (for example argon) (702) is held in a central cylinder (703) and surrounded by a jacket of another cryogen (for example liquid nitrogen) (706) in order to maintain the low temperature of the internal cylinder (703). The liquid nitrogen of this example is contained in the liquid nitrogen and liquid argon collector (707). Argon will freeze at liquid nitrogen temperatures into a solid plug (702), and this plug can then be slowly extruded, using an argon plug elevation platform (708), through the top of the internal cylinder (703). The upper surface of the argon plug acts as the target for the nebulized stream. Nebulized droplets will then rapidly impact the leading surface of the frozen argon plug target (702), resulting in very rapid freezing of the droplets. As this occurs, the frozen argon plug surface (702) will melt into liquid argon, and the flow of liquid argon away from the impact point will then carry the frozen droplet particles away from the center of the plug, to be collected in a liquid argon or a liquid argon/liquid nitrogen mixture contained by a liquid nitrogen and liquid argon collector (706) at the outer edge of the target plug.

Nebulized sample particles frozen using this method are easily recovered because they remain suspended in the liquefied primary refrigerant at the end of the freezing process. The primary refrigerant liquefies after absorbing heat from the sample, then washes the frozen sample droplets away from the active freezing contact site. Depending on the difference in density between the frozen sample particles and the liquefied refrigerant, the sample particles can be recovered 1) by gravity at the bottom of the refrigerant vessel, 2) by skimming or overflow after floating to the refrigerant surface, or 3) by filtration if suspended within the refrigerant. The ease of sample recovery is a distinct advantage over other prior-art methods, which require scraping frozen samples off cold metal surfaces, removing samples from porous or thin film plates, detaching samples from metal grids, or unsealing samples from tubes or metal canisters. Short or long-term storage of frozen nebulized samples is also greatly simplified by this freezing method, again because the sample remains within the liquefied primary refrigerant after freezing. The primary refrigerant is generally nonreactive and nontoxic, typically liquid nitrogen or a liquefied noble gas, so the frozen sample is subjected to no long-term adverse effects if it remains suspended in the primary refrigerant for storage. An additional advantage is that the sample remains at its freezing temperature indefinitely because there is no need to transfer to another container or medium for storage, so the risk of heating the sample above one of its glass or crystalline transition temperatures is minimized.

Solid or slushed cryogenic "gas" refrigerants used in this method may be noble gases (He, Ne, Ar, etc.) or common industrial cryogens (nitrogen) which are generally chemically nonreactive and nontoxic. This is especially useful when freezing organic or biological materials, or living cells, because the freezing samples come into direct contact with the refrigerants, and some of the refrigerant substance is expected to diffuse into the frozen samples. The use of nonreactive and nontoxic refrigerants is a significant advantage over methods that use organic solvents such as ethane, propane, and butane as liquid refrigerants. Frozen samples are heavily contaminated by these organic solvents, which poison the sample or require removal (usually by a less-toxic organic solvent). Use of noble gases, or in some instances nitrogen, is especially useful for "time stopping" experiments using samples of actively reacting chemicals.

Primary (solid-to-liquid phase) refrigerants and secondary refrigerants (those used to initially freeze the primary refrigerants) are typically inexpensive atmospheric or industrial cryogenic liquefied gases currently mass-produced by efficient industries. They include liquid nitrogen, liquid argon, and liquid helium, and can be extended to more exotic refrigerants such as liquid hydrogen, liquid neon, liquid oxygen, alcohol, or even chilled metals such as mercury. Most of the refrigerants are abundant, easy to ship and handle, and are inert, reducing the cost of purchasing or using the primary raw materials of the process. Waste products generated by the process, typically atmospheric gases or helium, are simply vented or recycled, or for hydrogen, simply burned to produce water vapor, so disposal costs of waste products are minimal or absent. The low cost of operation and the wide availability of raw materials makes this process less expensive than other hyper-rapid freezing methods. Most nebulizers are inexpensive pressure spray nozzles or common ultrasonic commercial devices. These relatively inexpensive items represent a significant cost advantage over currently used rapid freezing devices containing high pressure vessels, programmable electronic variable rate cooling systems, mechanical or electromagnetic sample plungers, or elaborate chemical preparation of samples. Another cost advantage of this freezing process is the absence of organic solvent or waste disposal—the refrigerants are simply recycled or are vented off into the atmosphere.

Component Variations

The following illustrations and paragraphs will describe some variations in the components of the freezing assembly.

Figure 8A:
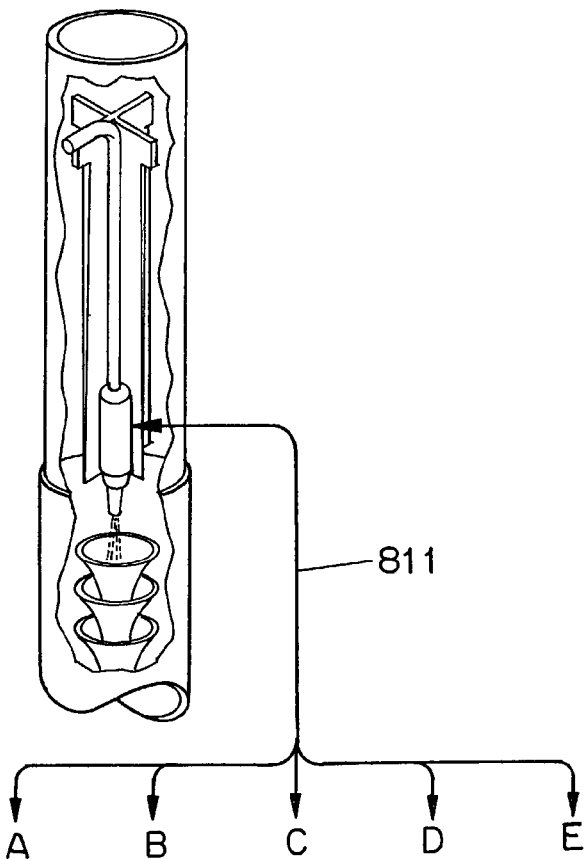
FIG. 8A is an illustration of several embodiments of the nebulizer device.
Figure 8B:
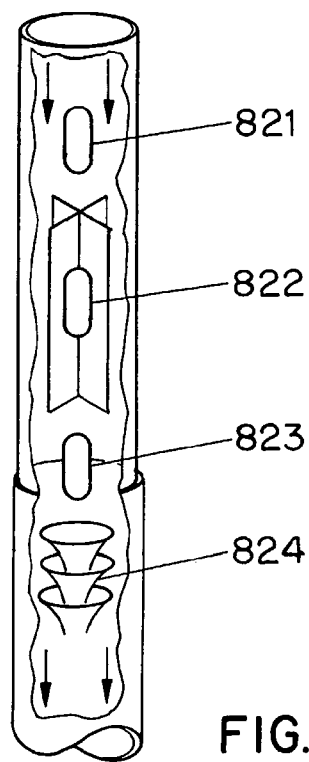
FIG. 8B illustrates several positions of the nebulizer device.

FIG. 8B illustrates several of the possible variations in the location of the nebulizer device (811). The fluid nebulizer can be located above (821), within (822), or below (823) the laminar flow section (400), in this case a radial vane assembly. If located upstream of the laminar flow section (400), nebulized particles are randomly distributed within the entering stream, which is then funneled into a laminar flow by the vanes (418) in the following section. The nebulizing device outlet itself can be located within (822) the laminar flow vanes (418), or may be located below (823) the flow vanes so that nebulized particles are injected directly into a laminar driving gas stream.

Various nebulizing devices can be used and are represented by letters in FIG. 8A. They include a flow cytometer (114/A) to generate a slow flow of exactly equal sized droplets, a gas driven nebulizer (B) (spray nozzle) which utilizes a high fluid pressure gradient at the nozzle tip to form droplets, an ultrasonic nebulizer (C), or a drip screen (D) where droplets are formed on the surface of a porous screen as gas flows through the holes in the screen. A vibrating diaphragm (E) is a lower frequency version of the ultrasonic nebulizer (C). Any of these nebulizers can be used in the freezing device as long as the size and shape of the portion which contains the emerging droplets does not interfere with the laminar flow of the driving gas.

Figure 9A:
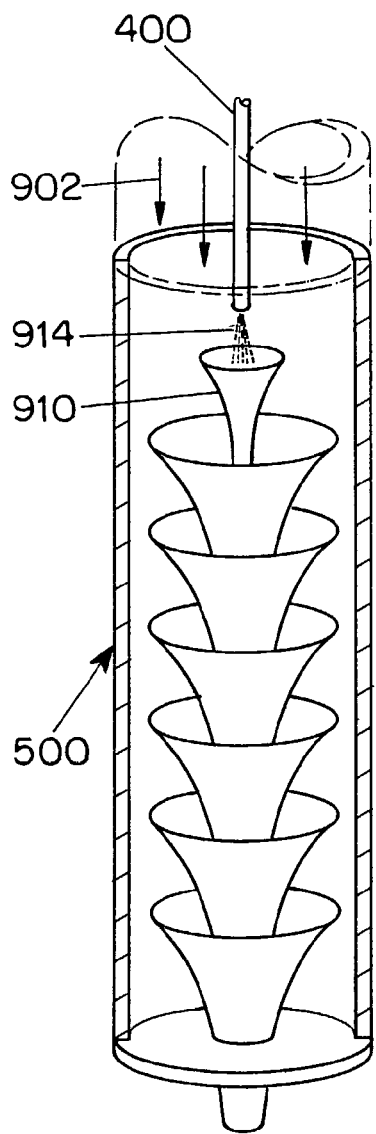
FIG. 9A illustrates an embodiment of the driving gas accelerator section.
Figure 9B:
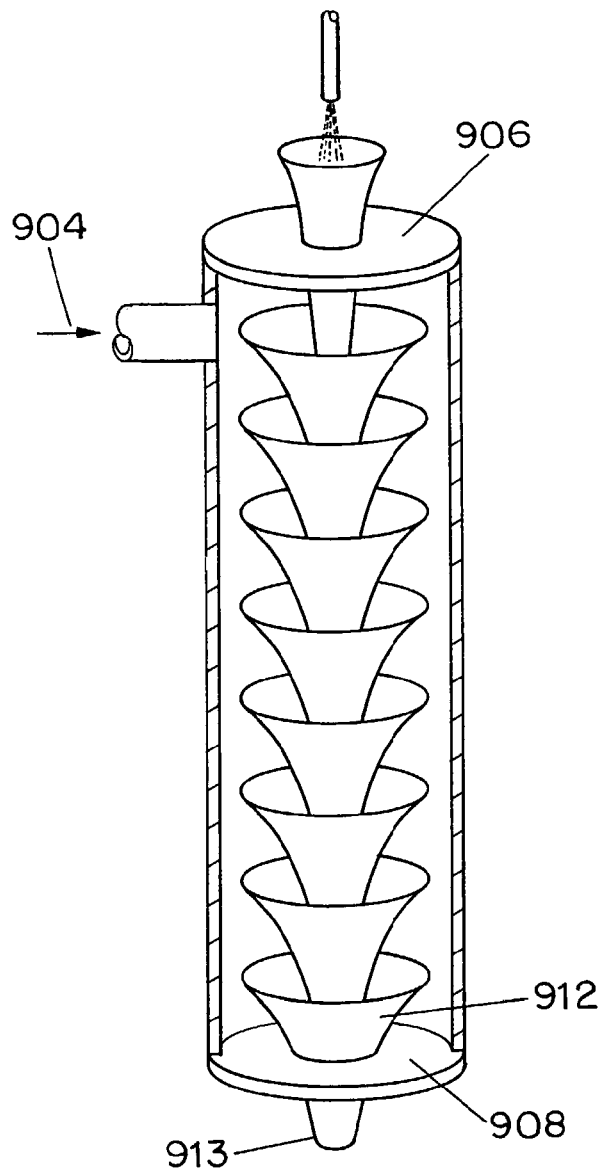
FIG. 9B illustrates an embodiment of the driving gas accelerator section.

Variations in the driving gas accelerator section (500) are illustrated in FIGS. 9A and 9B. The gas directly entering the first accelerator cone may be isolated from the ambient atmosphere by a relatively narrow diameter upstream laminar flow section (400). In this instance, the accelerator section (500) would require a separate source of gas (902), either ambient atmosphere or pressurized gas (904). A pressurized chamber surrounding the accelerator cones as illustrated in FIG. 9B would be sealed at the upstream (906) and downstream (908) sections so that no gas can leak around the first (910) or last (912) accelerator cone. This variation would also allow control of the type of gas, pressure of gas, and water content (humidity) of gas applied to the accelerator cones. Concentric flow of the driving gas jacketed around the laminar flow section (400) is illustrated by the open end section diagram in FIG. 9A.

Figure 9C:
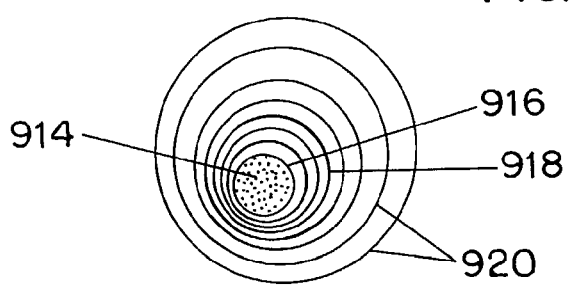
FIG. 9C illustrates and a cross section of an embodiment of the nebulized stream emerging from the last accelerator cone.

FIG. 9C illustrates the cross section of the nebulized stream emerging from the last accelerator cone, and it is essentially a view looking up facing the small end of the cone (913). The nebulized particle stream (914) is located at the center of the accelerated gas flow stream, with concentric layers of drive gas shown. The layer of drive gas immediately surrounding the nebulized stream (916) was acquired between the first and the second accelerator cone, and subsequent concentric layers of drive gas (918 and 920) moving away from the center were acquired from gas entering between subsequent accelerator cones progressing down toward the last cone. The initially very slow nebulized gas stream is accelerated to faster and faster velocities as each concentric layer of drive gas is acquired during the progression down the accelerator cone column. The maximum velocity of the nebulized stream is achieved when it exits the last accelerator cone (912).

Figure 10A:
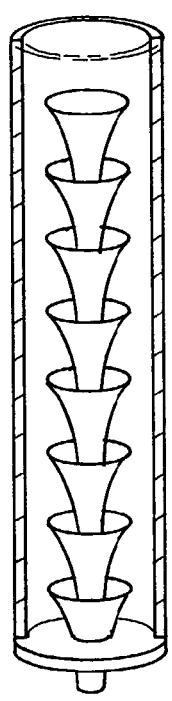
FIGS. 10A-10H illustrate several embodiments of the accelerator cone section.
Figure 10B:
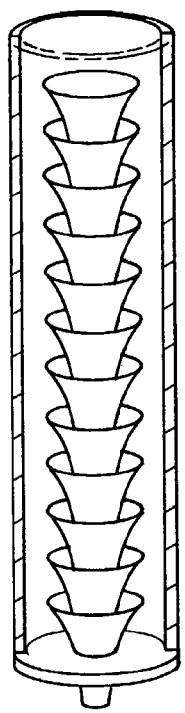
Figure 10C:
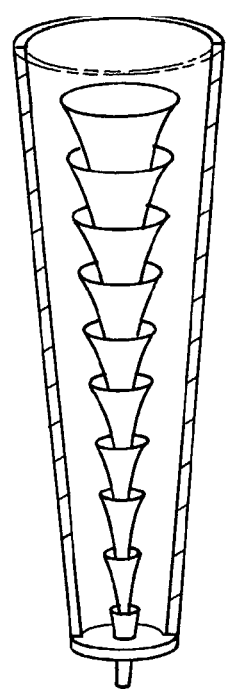
Figure 10D:
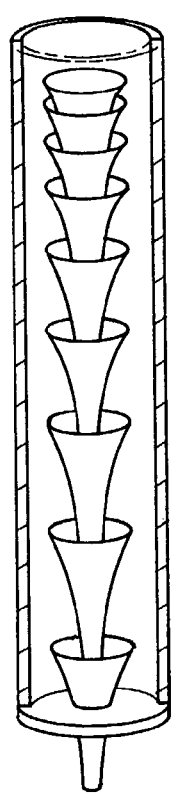
Figure 10E:
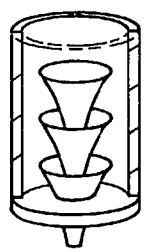
Figure 10F:
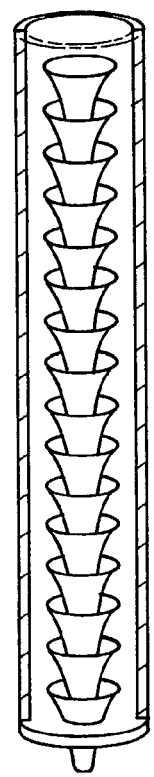
Figure 10G:
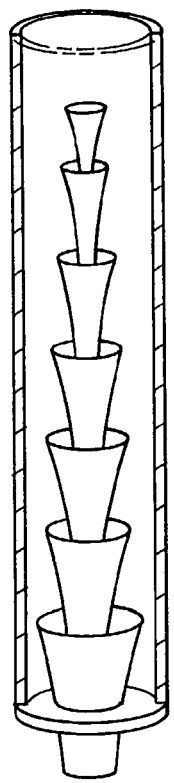
Figure 10H:
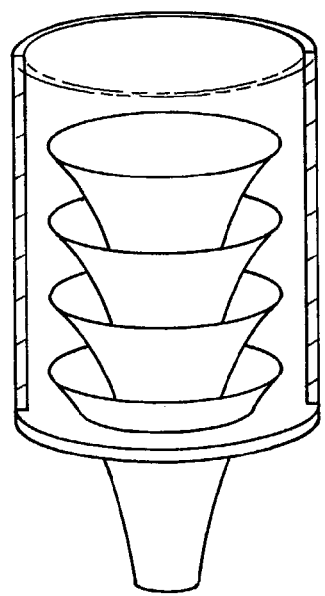

Additional variations in the accelerator cone section are illustrated by FIGS. 10A-10H. Different characteristics of the nebulized particle and drive gas stream are acquired by changes in the spacing of the nebulized cones, change in diameter of the driving gas container, length of the entire accelerator assembly, or total number of cones used. These variations are determined by the final application requirements of the nebulized stream. FIG. 10A is an illustration of widely spaced cones. FIG. 10B is an illustration of narrowly space cones. FIG. 10C is an illustration of tapering cone diameters. FIG. 10D is an illustration of variable cone spacing. FIG. 10E is an illustration of a short accelerator. FIG. 10F is an illustration of a long accelerator. FIG. 10G is an illustration of variable sizes of cones within the accelerator. FIG. 10H is an illustration of a wide accelerator.

Figure 11A:
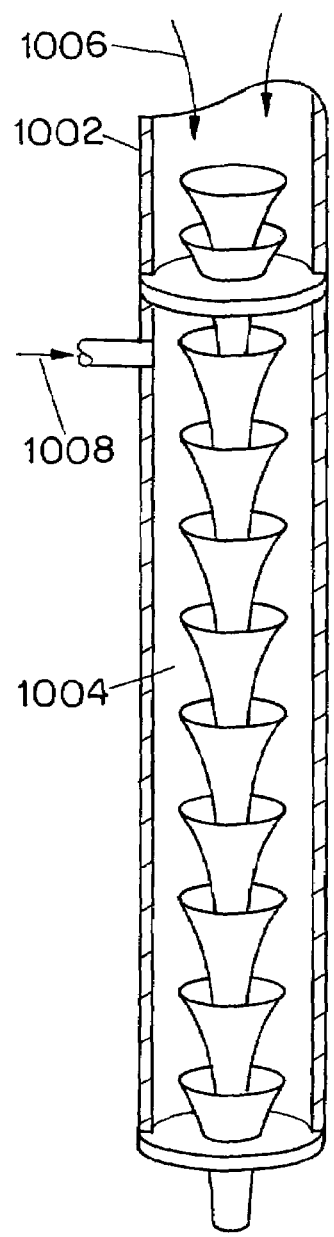
FIG. 11A is an illustration of an optional method to increase control of driving gas composition and pressure.
Figure 11B:
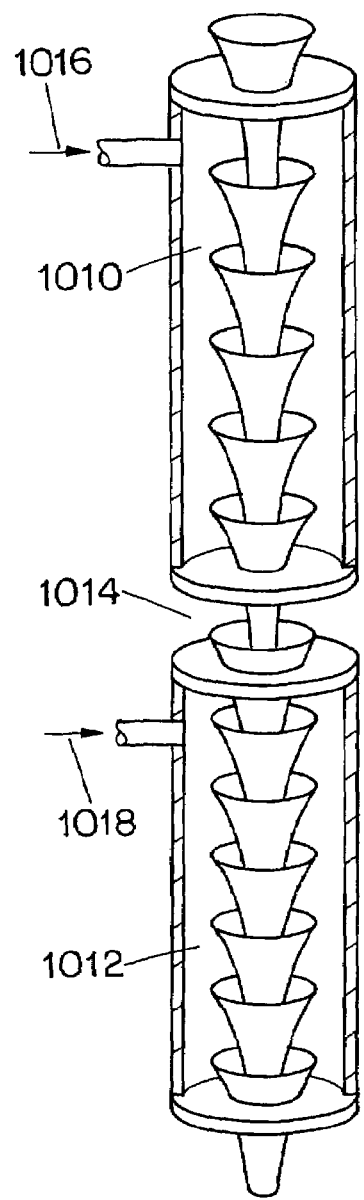
FIG. 11B is an illustration of an optional method to increase control of driving gas composition and pressure.
Figure 11C:
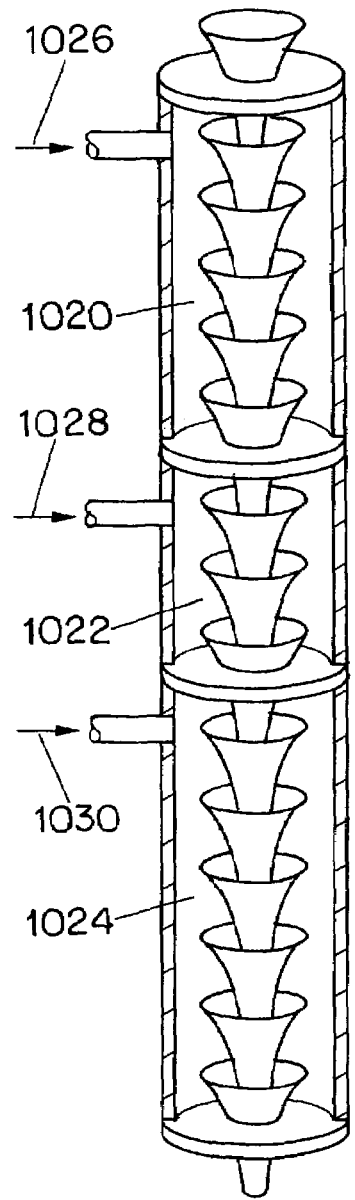
FIG. 11C is an illustration of an optional method to increase control of driving gas composition and pressure.
Figure 13A:
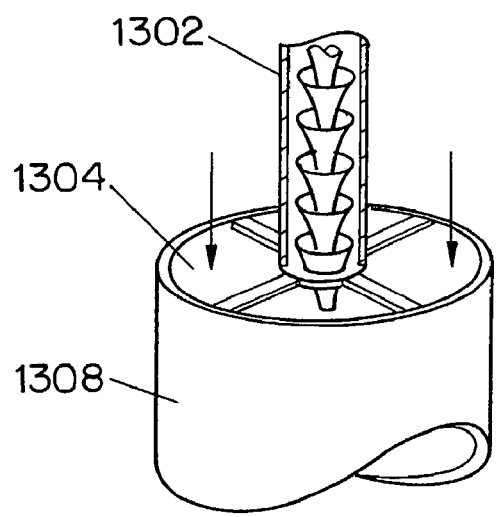
Figure 13B:
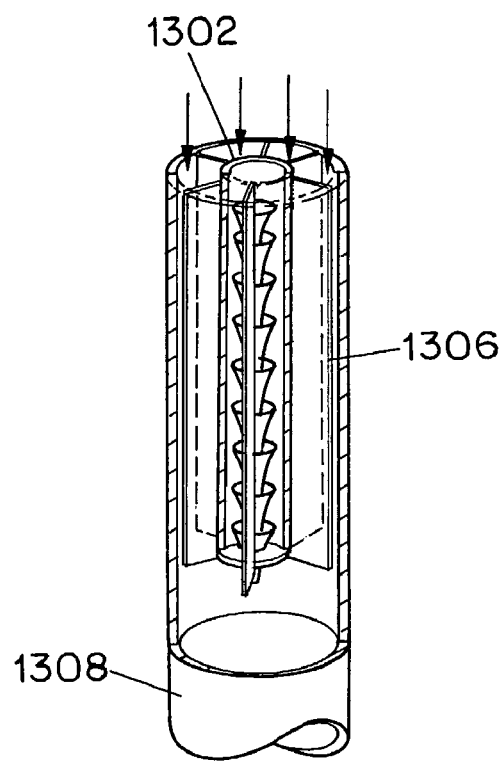
Figure 13C:
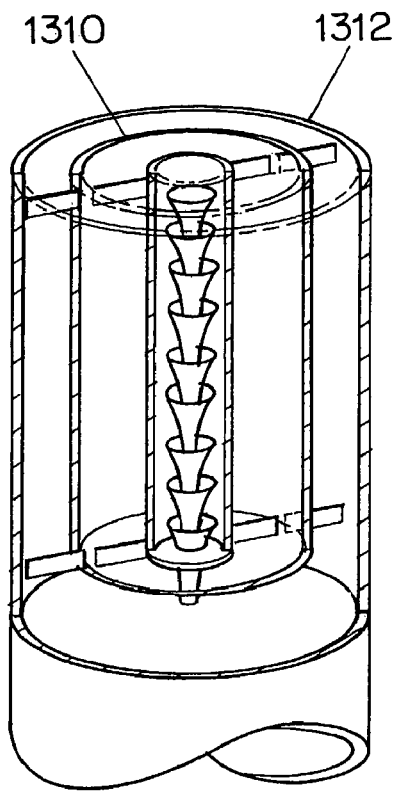
Figure 13D:
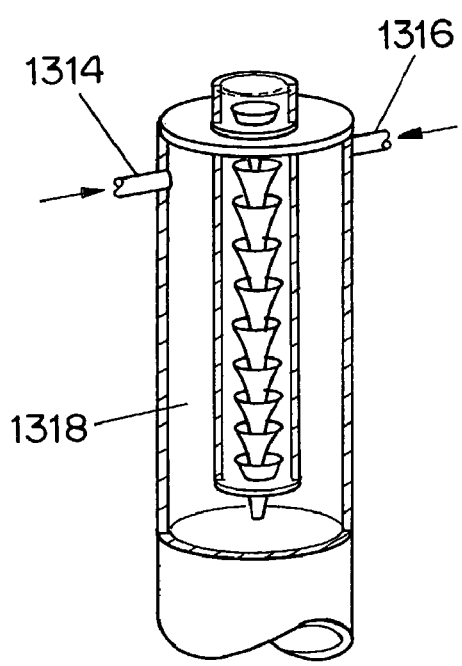
Figure 14A:
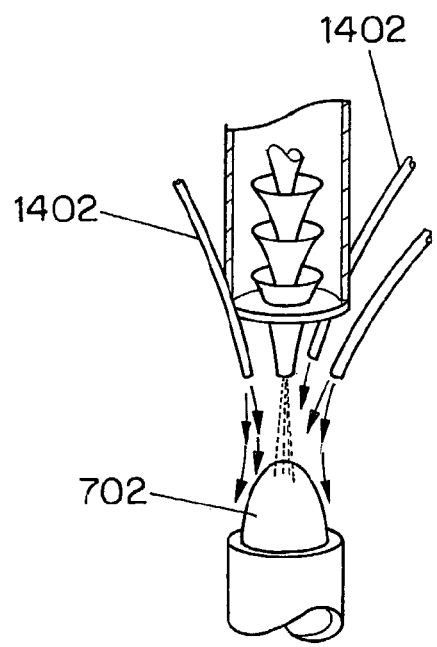
FIGS. 14A-14F illustrate several methods to control the nebulized stream direction in the freezing section just above the target.
Figure 14B:
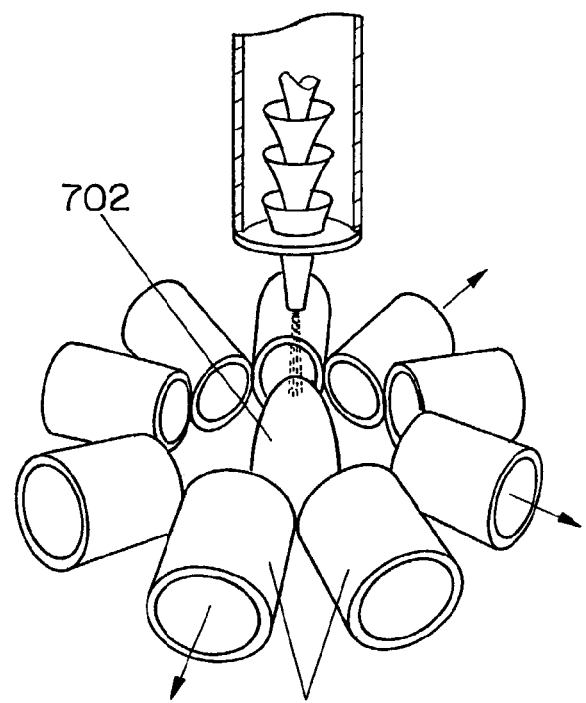
Figure 14C:
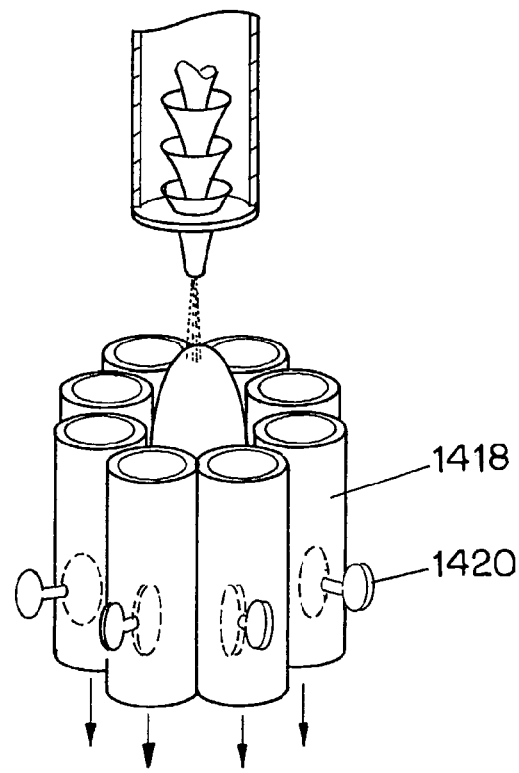
Figure 14D:
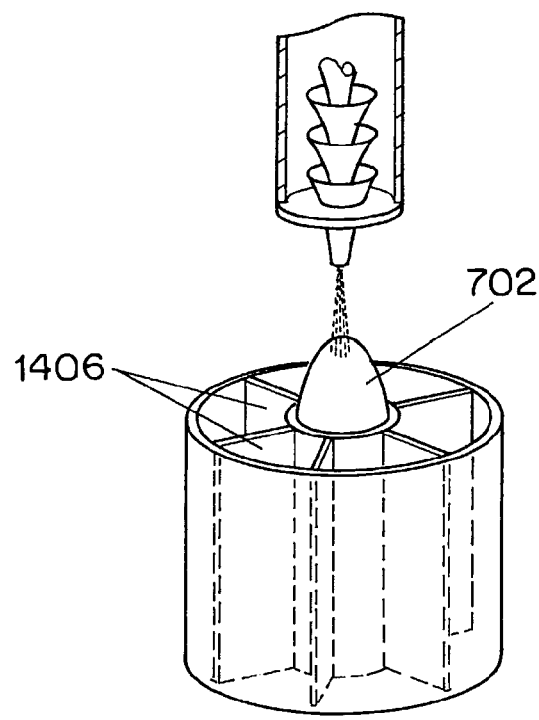
Figure 14E:
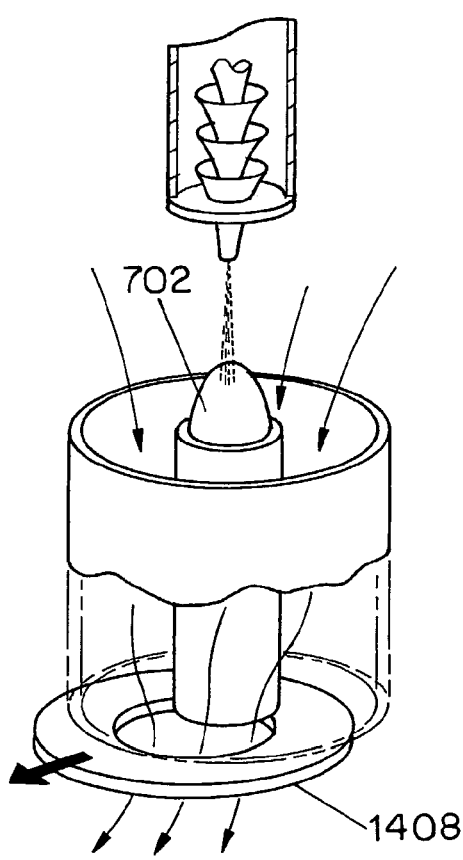
Figure 14F:
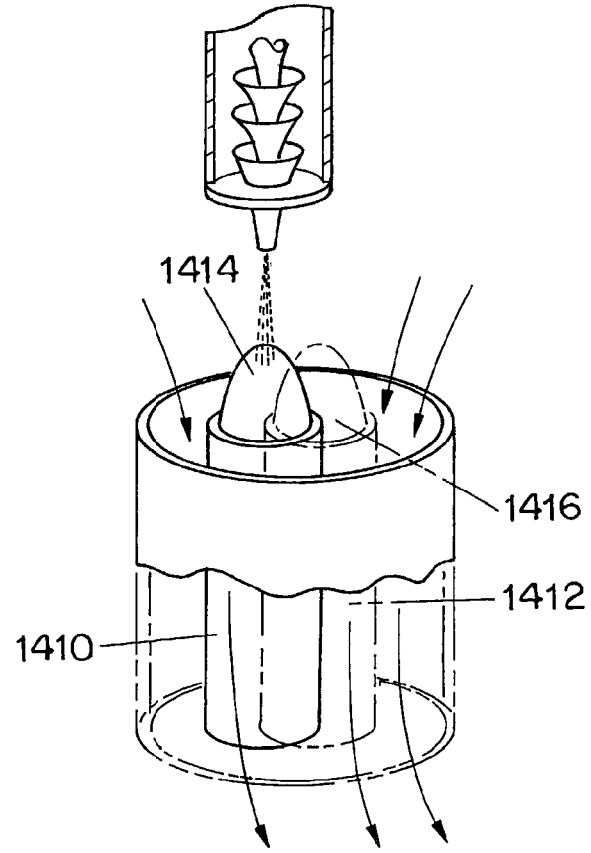
Figure 15G:
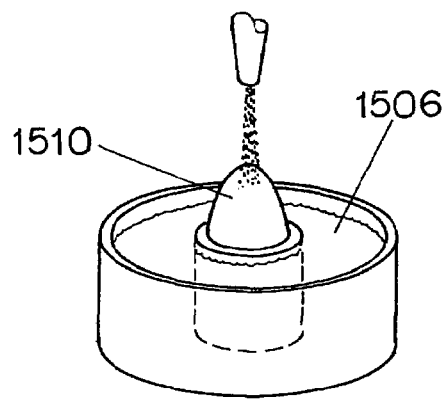
Figure 15H:
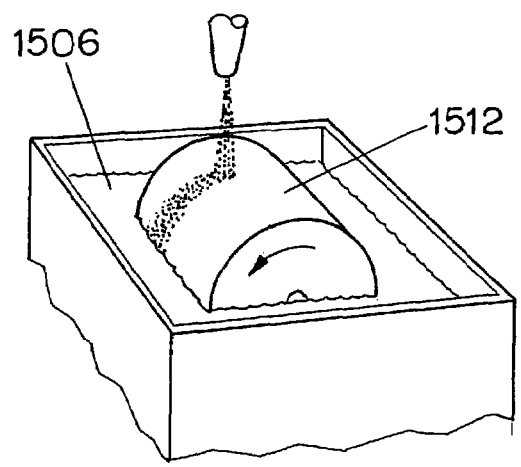
Figure 15I:
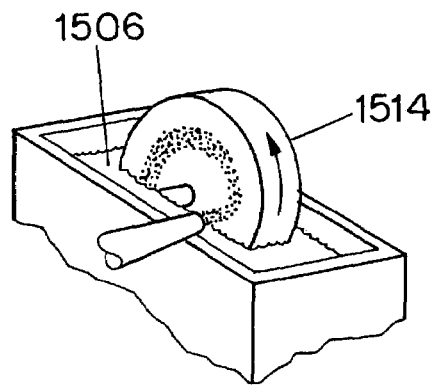
Figure 15J:
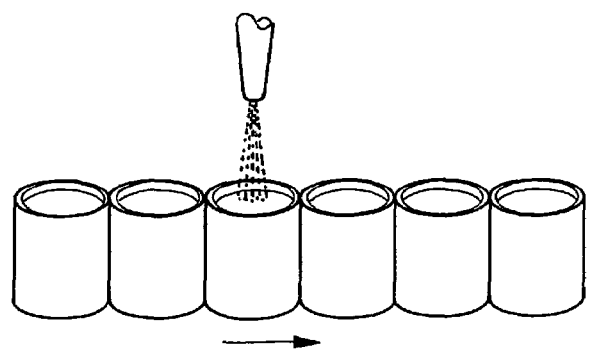

FIGS. 11A through 11C illustrate embodiments of the methods of dividing accelerator sections in order to increase control of the driving gas composition and pressure. The accelerator section (500) can be divided into several subsections aligned in serial fashion, with ambient gas gaps between sections, or with sections sealed together. An example of an application of this assembly would be to use a noble gas around a highly reactive stream of nebulized droplets, with the noble gas injected into the upper most accelerated section, followed by less expensive gasses applied to the outer layers of the emerging gas stream by injecting these gasses into the lowermost chambers of the accelerator section (500). FIG. 11A is an illustration of an embodiment of the accelerator section which is divided into two subsections (1002 and 1004). Ambient gas (1006) enters upper section (1002) and drive gas (1008) is applied to the enclosed layer (1004). FIG. 11B is an illustration of an embodiment of the accelerator section which is divided into two enclosed subsections (1010 and 1012), where a first drive gas (1016) is applied to the first enclosed subsection (1010) and a second drive gas (1018) is applied to a second enclosed section (1012), and ambient air is allowed to further drive the nebulized droplets into a third subsection (1014) which is open. FIG. 11C illustrates an embodiment of an accelerator section which is divided into three separate enclosed subsections. In this embodiment, each subsection (1020, 1022, and 1024) has a separate drive gas (1026, 1028, and 1030).

Various embodiments of the accelerator cones are illustrated in FIGS. 12A through 12P, with typically a single example of each cone type illustrated. For instance, the first cone type illustrated in FIG. 12A is a segment taken of a parabolic curve which is then rotated around a central axis to form the surface of the cone. The second cone type, illustrated in FIG. 12B, is a segment taken of a hyperbolic curve which is then rotated around a central axis to form the surface of the cone. The third cone type, illustrated in FIG. 12C, is a linear segment which is then rotated around a central axis to form the surface of the cone. By stacking several identical cones into an accelerator section, control of the laminar flow stream can be achieved for different specific applications. While FIG. 12D illustrates one of the most common cone shapes, other embodiments are illustrated in FIGS. 12E through 12I. FIG. 12A is an embodiment of a narrow cone. FIG. 12F is an embodiment of a wide cone. FIG. 12G is an embodiment of a tapered cone. FIG. 12H is an embodiment of a short cone. FIG. 12I is an embodiment of a long cone. In addition, FIG. 12M is a polygon shaped cone, and FIG. 12N is a cone having an offset. Other embodiments in this set of figures include vortex vanes on the inner or outer surface of the cone which rotate the driving gas as it emerges from the end of the cone. FIG. 12J is an illustration of an embodiment of internal vanes on a cone. FIG. 12K is an illustration of external vanes on a cone. FIG. 12L is an illustration of straight vanes on a cone. Fusion of two separate nebulized gas streams can also be done using this method, or a single nebulized gas stream can be divided into two or more gas streams using sequential changes in the shape of the cones as they progress down the accelerator section. FIG. 12O is an illustration of a split stream embodiment of a cone stack assembly. FIG. 12P is an illustration of a fused stream embodiment of a cone stack assembly.

Variations in the control of the acquired ambient gas for the freezing section are illustrated by FIGS. 13A through 13F. These embodiments of the invention include simple ports for entry of the gas at the top of the freezing section (FIGS. 13A and 13B). In FIG. 13A the simple ports (1304) for entry are located immediately above the freezing section (1308), allowing gas to travel parallel to accelerator section 1302. FIG. 13A illustrates gas flowing into vanes (1306) arranged radially around the accelerator section (1302). FIG. 13C illustrates acquisition of laminar flow of the ambient gas by vanes placed in a concentric cylinders (1310 and 1312) around the accelerator section. The gas content and pressure can also be controlled using a pressurized enclosed cylinder chamber (1318) as illustrated in FIG. 13D. In FIG. 13D, gas enters the cylinder chamber (1318) through entry points 1314 and 1316. Better laminar flow around the emerging drive gas nebulized stream (1326) from the lower end of the last accelerator cone can be achieved by tapering the segment surrounding this exit point as illustrated by the tapered end (1322) of FIG. 13F. FIG. 13E shows an emerging drive gas nebulized stream (1324) flowing around a flat end (1320) exit point of the lower end of the last accelerator cone.

The control of the nebulized stream direction in the freezing section just above the target (702) can be achieved by various embodiments of the method of the invention illustrated In FIGS. 14A through 14F. The flow of gas away from the nebulized stream just before and at the point of target impact can be done using various angled stream tubes (1402), radial removal of the gas through radial gas removal tubes (1404), or differential control of the diameter and shape of the ambient gas exit port using coaxial cylinders. FIG. 14C illustrates an embodiment of the invention which uses in-line gas removal tubes (1418) which are controlled with control valves (1420). Encouragement of laminar flow beyond the target point (702) can also be done to minimize the breakup of laminar droplet flow into chaotic flow using flow vanes (1406) in the outer portion of the gas freezing section, as illustrated by FIG. 14D. FIG. 14E illustrates an embodiment of the invention with an offset axis ring (1408) which can be moved in the X and Y directions to further control the ambient gas flow rate around the inner cylinder containing the target (702), and thus the direction and impact point of the laminar flow stream above. FIG. 14F illustrates an embodiment of the invention where the target (702) is movable. The inner cylinder is in a first position (1410) supporting the target in its first position (1414) and then moves to a second position (1412), thus moving the target to a second position (1416) as well.

Various embodiments of the type of target for the nebulized stream are illustrated by FIGS. 15A through 15J. A primary application of this device is to rapidly freeze small droplets of fluid in the nebulized stream by using a very cold target. The target can be cooled by a cryogen located immediately below the target plate (1502) as shown in FIG. 15A. As illustrated by FIG. 15B, the target also could be cooled by circulating flow of a cryogen (1504) within the target plate (1502). The target itself can be of various shapes more compatible with laminar flow including a dome shape like the one illustrated in FIG. 15C or cone shaped as in FIG. 15D. The cryogen pool (1506) can surround a perpetually cooled target (1502) at its center as illustrated in FIG. 15E, or the target may be a cryogenic liquid (1506) itself, which is illustrated by FIG. 15F, such as liquid nitrogen or liquid helium. A slush of cryogen would enhance freezing because its phase change from solid to liquid at the impact point would minimize the formation of an insulating gas envelop around the nebulized droplets (1508). The same would occur with a solidified frozen gas target (1510), shown in FIG. 15G, which would melt at the nebulized droplet impact point. The renewable surface of the target can be achieved as in FIG. 15H by a rotating drum (1512) method, the rotating disk (1514) method of FIG. 15I, or a fraction sample collector which would be used in conjunction with a chromatography or fractionation device above the nebulizer illustrated by the fractionated targets of FIG. 15J.

In order to increase the production of frozen particles, the number of freezing units could be increased, and high outputs could be achieved by running a large number of identical freezing units in parallel.

The invention claimed is:

1. A method comprising:
   transforming a liquid into very small drops;
   creating a droplet gas stream by surrounding the very small drops with a laminar flow of gas, said
   droplet gas stream traveling at a first rate of speed and having a first width;
   accelerating the droplet gas stream to a second rate of speed by narrowing the droplet gas stream to a second width, said second width being narrower than the first width and said second rate of speed being at a higher velocity than the first rate of speed;
   directing the droplet gas stream traveling at the second rate of speed onto a refrigerant which is at least partially solidified.

2. The method of claim 1 wherein said refrigerant is solid.

3. The method of claim 1 wherein said refrigerant is undergoing sublimation.

4. The method of claim 1 wherein said refrigerant is a slush comprising a mixture of solid and liquid.

5. The method of claim 4 wherein said solid and liquids are the same element or compound.

6. The method of claim 4 wherein said solid and liquids are different elements or compounds.

7. A method comprising:
   transforming a liquid into very small drops;
   creating a droplet gas stream by surrounding the very small drops with a laminar flow of gas, said
   droplet gas stream traveling at a first rate of speed and having a first width;
   accelerating the droplet gas stream to a second rate of speed by confining the droplet gas stream to a second width, said second width being narrower than the first width and said second rate of speed being at a higher velocity than the first rate of speed;
   directing the droplet gas stream traveling at the second rate of speed onto a refrigerant which is at least partially solidified;
   rapidly freezing the very small drops portion of the droplet gas stream upon contact with the refrigerant creating very small frozen particles;
   collecting the very small frozen particles from the refrigerant; and
   directing the gas portion of the droplet gas stream away from the refrigerant.

8. The method of claim 7 wherein said refrigerant is solid.

9. The method of claim 7 wherein said refrigerant is undergoing sublimation.

10. The method of claim 7 wherein said refrigerant is a slush comprising a mixture of solid and liquid.

11. The method of claim 8 wherein said solid and liquids are the same element or compound.

12. The method of claim 8 wherein said solid and liquids are different elements or compounds.

13. The method of claim 7 wherein after the very small frozen particles are collected from the refrigerant, the gas portion of the droplet gas stream is directed into a vacuum.

14. A method comprising:
    transforming a liquid into very small drops;
    creating a droplet gas stream by surrounding the very small drops with a laminar flow of gas, said
    droplet gas stream traveling at a first rate of speed and having a first width;
    narrowing the droplet gas stream to a second width and accelerating the droplet gas stream to a second rate of speed by directing the droplet gas stream through a first open end of an open ended cone,
    said open ended cone also having a second open end, the first open end and second open end each having a width, the width of the first open end being wider than the width of the second open end,
    said second width of the droplet gas stream being narrower than the first width of the droplet gas stream and said second rate of speed being at a higher velocity than the first rate of speed;
    directing the droplet gas stream traveling at the second rate of speed onto a refrigerant which is at least partially solidified.

15. The method of claim 14 wherein said refrigerant is solid.

16. The method of claim 14 wherein said refrigerant is undergoing sublimation.

17. The method of claim 14 wherein said refrigerant is a slush comprising a mixture of solid and liquid.

18. The method of claim 17 wherein said solid and liquids are the same element or compound.

19. The method of claim 17 wherein said solid and liquids are different elements or compounds.

20. A method comprising:
    transforming a liquid into very small drops;
    creating a droplet gas stream by surrounding the very small drops with a laminar flow of gas, said
    droplet gas stream traveling at a first rate of speed and having a first width;
    narrowing the droplet gas stream to a second width and accelerating the droplet gas stream to a second rate of speed by directing the droplet gas stream through a first open end of a first open ended cone,
    said first open ended cone also having a second open end, the first open end and second open end each having a width, the width of the first open end being wider than the width of the second open end,
    said second width of the droplet gas stream being narrower than the first width of the droplet gas stream and said second rate of speed being at a higher velocity than the first rate of speed;
    narrowing the droplet gas stream to a third width and accelerating the droplet gas stream to a third rate of speed by directing the droplet gas stream through a first open end of a second open ended cone,
    said second open ended cone also having a second open end, the first open end and second open end each having a width, the width of the first open end being wider than the width of the second open end,
    said third width of the droplet gas stream being narrower than the second width of the droplet gas stream and said third rate of speed being at a higher velocity than the second rate of speed;

directing the droplet gas stream traveling at the third rate of speed onto a refrigerant which is at least partially solidified.

21. The method of claim 20 wherein said refrigerant is solid.

22. The method of claim 20 wherein said refrigerant is undergoing sublimation.

23. The method of claim 20 wherein said refrigerant is a slush comprising a mixture of solid and liquid.

24. The method of claim 23 wherein said solid and liquids are the same element or compound.

25. The method of claim 23 wherein said solid and liquids are different elements or compounds.

26. A method comprising:
transforming a liquid into very small drops;
creating a droplet gas stream by surrounding the very small drops with a laminar flow of gas, said
droplet gas stream traveling at a first rate of speed and having a first width;
narrowing the droplet gas stream to a second width and accelerating the droplet gas stream to a second rate of speed by directing the droplet gas stream through a first open end of a first open ended cone,
said first open ended cone also having a second open end, the first open end and second open end each having a width, the width of the first open end being wider than the width of the second open end,
said second width of the droplet gas stream being narrower than the first width of the droplet gas stream and said second rate of speed being at a higher velocity than the first rate of speed;
narrowing the droplet gas stream to a third width and accelerating the droplet gas stream to a third rate of speed by directing the droplet gas stream through a first open end of a second open ended cone,
said second open ended cone also having a second open end, the first open end and second open end each having a width, the width of the first open end being wider than the width of the second open end,
said third width of the droplet gas stream being narrower than the second width of the droplet gas stream and said third rate of speed being at a higher velocity than the second rate of speed;
narrowing the droplet gas stream to a fourth width and accelerating the droplet gas stream to a fourth rate of speed by directing the droplet gas stream through a first open end of a third open ended cone,
said third open ended cone also having a second open end, the first open end and second open end each having a width, the width of the first open end being wider than the width of the second open end,
said fourth width of the droplet gas stream being narrower than the third width of the droplet gas stream and said fourth rate of speed being at a higher velocity than the third rate of speed;
directing the droplet gas stream traveling at the fourth rate of speed onto a refrigerant which is at least partially solidified.

27. The method of claim 26 wherein said refrigerant is solid.

28. The method of claim 26 wherein said refrigerant is undergoing sublimation.

29. The method of claim 26 wherein said refrigerant is a slush comprising a mixture of solid and liquid.

30. The method of claim 29 wherein said solid and liquids are the same element or compound.

31. The method of claim 30 wherein said solid and liquids are different elements or compounds.

32. A method comprising:
transforming a liquid into very small drops;
creating a droplet gas stream by surrounding the very small drops with a laminar flow of gas, said
droplet gas stream traveling at a first rate of speed and having a first width;
accelerating the droplet gas stream to a second rate of speed by narrowing the droplet gas stream to a second width, said second width being narrower than the first width and said second rate of speed being at a higher velocity than the first rate of speed;
accelerating the droplet gas stream to a third rate of speed by narrowing the droplet gas stream to a third width, said third width being narrower than the second width and said thrid rate of speed being at a higher velocity than the second rate of speed;
directing the droplet gas stream traveling at the third rate of speed onto a refrigerant which is at least partially solidified.

33. The method of claim 32 wherein said refrigerant is solid.

34. The method of claim 33 wherein said refrigerant is undergoing sublimation.

35. The method of claim 34 wherein said refrigerant is a slush comprising a mixture of solid and liquid.

36. The method of claim 35 wherein said solid and liquids are the same element or compound.

37. The method of claim 35 wherein said solid and liquids are different elements or compounds.

38. A method comprising:
transforming a liquid into very small drops;
creating a droplet gas stream by surrounding the very small drops with a laminar flow of gas, said
droplet gas stream traveling at a first rate of speed and having a first width;
accelerating the droplet gas stream to a second rate of speed by narrowing the droplet gas stream to a second width, said second width being narrower than the first width and said second rate of speed being at a higher velocity than the first rate of speed;
accelerating the droplet gas stream to a third rate of speed by narrowing the droplet gas stream to a third width, said third width being narrower than the second width and said third rate of speed being at a higher velocity than the second rate of speed;
accelerating the droplet gas stream to a fourth rate of speed by narrowing the droplet gas stream to a fourth width, said fourth width being narrower than the third width and said fourth rate of speed being at a higher velocity than the third r ate of speed;
directing the droplet gas stream traveling at the fourth rate of speed onto a refrigerant which is at least partially solidified.

39. The method of claim 38 wherein said refrigerant is solid.

40. The method of claim 38 wherein said refrigerant is undergoing sublimation.

41. The method of claim 38 wherein said refrigerant is a slush comprising a mixture of solid and liquid.

42. The method of claim 41 wherein said solid and liquids are the same element or compound.

43. The method of claim 41 wherein said solid and liquids are different elements or compounds.

44. An apparatus for freezing a stream of small liquid droplets, said apparatus comprising:

a source of gas flow attached to a freezing assembly;

said freezing assembly comprising:

a gas stream directional section having a first end connected to the source of gas flow and a second end connected to a laminar flow vane section, said laminar flow vane section having a first end connected to the gas stream directional section and a second end connected to an accelerator section, said accelerator section having a first end connected to the laminar flow vane section and a second end connected to a freezing section, said freezing section comprising:

a target for the stream of small liquid droplets, at least three radial gas collectors, said gas collectors being parallel with the target, and a cryogen container and collector.

45. The apparatus of claim 44 wherein the gas stream directional section has a telescoping variable length.

46. The apparatus of claim 44 wherein the laminar flow vane section comprises:

a radial vane having at least three arms positioned inside a cylindrical tube, said cylindrical tube being connected at a first end to the gas stream directional section and a second end connected to the accelerator section.

47. The apparatus of claim 44 wherein the accelerator section comprises:

a hollow cylinder with first and second ends corresponding to the first and second ends of
the accelerator section;

at least one opened ended cone positioned inside the hollow cylinder, said open ended cone having a first end and a second end, each end having a width, wherein width of the first end is wider than the width of the second end, the first end of the open ended cone positioned closer to the laminar flow vane section than the second end of the open ended cone; and at least one spacing vane, said spacing vane being located between the at least one open ended cone and hollow cylinder.

48. The apparatus of claim 44 wherein a flow filter is positioned between the source of gas flow and the freezing assembly.

49. The apparatus of claim 44 wherein a humidifier is positioned between the source of gas flow and the freezing assembly.

50. The apparatus of claim 44 wherein a control valve is positioned between the source of gas flow and the freezing assembly.

51. The apparatus of claim 44 wherein a nebulizer is located between the gas stream directional section and the laminar flow section.

52. The apparatus of claim 44 wherein a nebulizer is located within the laminar flow section.

53. The apparatus of claim 44 wherein a nebulizer is located between the laminar flow section and the accelerator section.

* * * * *